(12) United States Patent
Moszner et al.

(10) Patent No.: US 8,829,067 B2
(45) Date of Patent: Sep. 9, 2014

(54) POLYMERIZABLE COMPOSITIONS WITH INITIATORS CONTAINING SEVERAL GE ATOMS

(75) Inventors: Norbert Moszner, Triesen (LI); Frank Zeuner, Schellenberg (LI); Robert Liska, Vienna (AT); Volker M. Rheinberger, Vaduz (LI); Iris Lamparth, Grabs (CH); Urs Karl Fischer, Arbon (CH)

(73) Assignee: Ivoclar Vivadent AG, Schaan (LI)

( * ) Notice: Subject to any disclaimer, the term of this patent is extended or adjusted under 35 U.S.C. 154(b) by 953 days.

(21) Appl. No.: 12/276,030

(22) Filed: Nov. 21, 2008

(65) Prior Publication Data

US 2009/0239967 A1 Sep. 24, 2009

(30) Foreign Application Priority Data

Mar. 20, 2008 (EP) ..................................... 08102841

(51) Int. Cl.
| | |
|---|---|
| *G03F 7/029* | (2006.01) |
| *C08F 4/44* | (2006.01) |
| *C07F 7/00* | (2006.01) |
| *C08F 4/16* | (2006.01) |
| *A61K 6/00* | (2006.01) |
| *C08F 4/72* | (2006.01) |
| *A61K 6/083* | (2006.01) |
| *C08F 2/50* | (2006.01) |

(52) U.S. Cl.
CPC ... *C08F 2/50* (2013.01); *C08F 4/16* (2013.01); *A61K 6/0017* (2013.01); *C08F 4/72* (2013.01); *A61K 6/0023* (2013.01); *A61K 6/083* (2013.01); *C08F 4/44* (2013.01)
USPC ................................ 522/66; 526/190; 556/87

(58) Field of Classification Search
USPC ................................ 522/66; 556/87; 526/190
See application file for complete search history.

(56) References Cited

U.S. PATENT DOCUMENTS

| | | | |
|---|---|---|---|
| 4,457,818 A | 7/1984 | Denyer et al. | |
| 4,525,256 A | 6/1985 | Martin | |
| 6,043,361 A | 3/2000 | Evans et al. | |
| 6,096,903 A | 8/2000 | Moszner et al. | |
| 6,344,556 B1 | 2/2002 | Evans et al. | |
| 6,479,592 B2 | 11/2002 | Rheinberger et al. | |
| 7,365,222 B2 | 4/2008 | Moszner et al. | |
| 2007/0287792 A1* | 12/2007 | Moszner et al. | 524/556 |
| 2008/0076847 A1 | 3/2008 | Moszner et al. | |

FOREIGN PATENT DOCUMENTS

| | | | |
|---|---|---|---|
| DE | 41 33 494 A1 | 4/1993 | |
| DE | 199-03-177 A1 | 7/2007 | |
| EP | 0 405 786 A2 | 1/1991 | |
| EP | 1 247 843 A2 | 10/2002 | |
| GB | 1 408 265 | 10/1975 | |
| GB | 1 429 806 A1 | 3/1976 | |
| JP | 07-165769 | * 6/1995 | ................ C07F 7/30 |
| WO | 01/51533 A1 | 7/2001 | |
| WO | 2005/086911 A2 | 9/2005 | |

OTHER PUBLICATIONS

Diederichsen et al.; Bimolecular reactiosn of alkyl halides and acylgermanes: formation of ketone, diketoens, and other products by radical-radical reaction; J. Organo. Met. Chem., 531 (1997) 9-12.*
Hayashi et al., Machine English translation of JP 07-165769 (Jun. 1995).*
Edward Piers and René M. Lemieux, Organometallics, 1998, 17 (19), 4213-4217.*
Olga Ekkert, Gerald Kehr, Roland Fröhlich, and Gerhard Erker, Journal of the American Chemical Society, 2011, 133 (12), 4610-4616.*
Maria L. Roldán, Silvia A. Brandán, Sarah L. Masters (née Hinchley), Derek A. Wann, Heather E. Robertson, David W. H. Rankin and Aída Ben Altabef, The Journal of Physical Chemistry A, 2009, 113 (17), 5195-5204.*
Stefan Marchart, Johann Mulzer, and Valentin S. Enev, Organic Letters, 2007, 9 (5), 813-816.*
Young-Taek Hong, Seok-Keun Yoon, Suk-Ku Kang, Chan-Mo Yu, European Journal of Organic Chemistry, 2004 (22), 4628-4635.*
Paul A. Deck, Travis S. Fisher, and J. Sloan Downey, Organometallics, 1997, 16 (6), 1193-1196.*
Ulrich Iserloh and Dennis P. Curran, The Journal of Organic Chemistry, 1998, 63 (14), 4711-4716.*
Scott A. Larkin, Jeffery T. Golden, Pamela J. Shapiro, Glenn P. A. Yap, David Ming Jin Foo, and Arnold L. Rheingold, Organometallics, 1996, 15 (9), 2393-2398.*
Yamamoto et al., "Preparation of Substituted Benzoyltrimethylsilanes and -germanes by the Reaction of Benzoyl Chlorides with Hexamethyldisilane or -digermane in the Presence of Palladium Complexes as Catalysts," Organometallics 6:974-979 (1987).

(Continued)

*Primary Examiner* — Liam J Heincer
(74) *Attorney, Agent, or Firm* — Ann M. Knab; Thad McMurray

(57) ABSTRACT

Composition with at least one polymerizable binder and one polymerization initiator, which contains at least one acylgermanium compound according to general Formula (I),

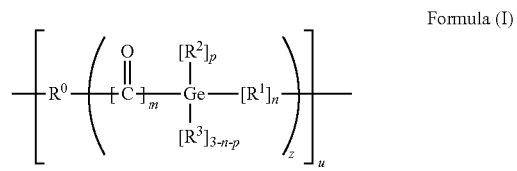

Formula (I)

and the use of acylgermanes of Formula (I) as initiators for radical polymerization or for the preparation of dental restorations.

23 Claims, No Drawings

(56) References Cited

OTHER PUBLICATIONS

Castel et al., "New (Diarylgermyl)lithiums," Organometallics 9:205-210 (1990).
Nishimura et al., "Synthesis of Acyltrialkylgermanes and Reactions with Carbon Nucleophiles," J. Chem. Soc. Perkin Trans. 1589-1594 (1994).
Brook et al., "Synthesis of Silyl and Germyl Ketones," J. Am. Chem. Soc. 89(2):431-434 (1967).
Sharma et al., "Organometalloidal Derivatives of the Transition Metals, XXVII. Chemical and Structural Investigations on (ferrocenylacyl)germanes," J. Organomet. Chem. 409:321-330 (1991).
Fouassier, eds., Radiation Curing in Polymer Science and Technology, vol. II, London and New York, NY:Elsevier Applied Science (1993).

* cited by examiner

POLYMERIZABLE COMPOSITIONS WITH INITIATORS CONTAINING SEVERAL GE ATOMS

This application claims the benefit of European Patent Application Serial No. 08102841.7, filed Mar. 20, 2008, which is hereby incorporated by reference in its entirety.

FIELD OF THE INVENTION

The present invention relates to polymerizable compositions which contain an acylgermanium compound with several germanium atoms as polymerization initiator. The compositions are particularly suitable for the preparation of adhesives, coatings, cements, composites, pre-shaped parts such as rods, plates, disks or lenses etc. and in particular dental materials.

BACKGROUND OF THE INVENTION

The initiator used plays a decisive role in the curing of polymerizable resins. Upon irradiation, photoinitiators absorb UV or visible light and form the polymerization-initiating species. In the event of radical polymerization these are free radicals. The photoinitiators are divided into two classes based on the chemical mechanism of radical formation.

Norrish type I photoinitiators form free radicals upon irradiation by unimolecular bond cleavage. Upon irradiation, Norrish type II photoinitiators undergo a bimolecular reaction wherein the excited photoinitiator reacts with a second molecule, the coinitiator, and forms the polymerization-initiating radicals by electron and proton transfer or direct hydrogen abstraction. Type I and type II photoinitiators are used for UV light curing; to date almost exclusively type II photoinitiators are used for the visible light range.

UV curing is characterized by a high reaction rate and is frequently used for the coatings of different substrates such as e.g. wood, metal or glass. Thus for example in EP 1 247 843 a UV-curing coating material is described in which type I photoinitiators such as diethoxyphenylacetophenone or acylphosphine oxide are used.

WO 01/51533 describes a UV-curing wood-coating material in which acylphosphine oxides, α-hydroxyalkylphenones or α-dialkoxyacetophenones are likewise used as photoinitiators. Above all, transparent coatings with low layer thickness can be UV-cured due to the low wavelength of the UV light; however, the limit of UV curing is reached with pronounced shading or pigmentation and greater layer thicknesses. Such resins cure only incompletely with UV light. Moreover, with pigmented compositions an absorption range must be found for the photoinitiator in which the pigment absorbs only weakly.

If greater through-curing depths are required, such as for example in the curing of light-curing dental filling materials, visible light is usually used for irradiation. The photoinitiator system most frequently used for this is a combination of an α-diketone with an amine coinitiator as is described in GB 1 408 265.

Dental compositions in which this photoinitiator system is used are disclosed e.g. in U.S. Pat. Nos. 4,457,818 or 4,525,256, wherein camphorquinone is preferably used an α-diketone. Camphorquinone has an absorption maximum at a wavelength of 468 nm. As a result camphorquinone displays a strong yellow colouring with the disadvantage that materials initiated with camphorquinone/amine have a noticeable yellow cast after curing. This is very disadvantageous in particular in the case of bright white shades of the fully polymerized material.

A further disadvantage of type TI photoinitiators is that they lead to the formation of a sticky surface layer upon polymerization. This so-called inhibition layer is attributable to the inhibition of the radical polymerization by oxygen in air.

EP 0 405 786 A2 discloses initiators based on silicon, germanium or tin which are said to be suitable for the mass polymerization of acrylic monomers in an extruder. The initiators are used together with co-catalysts such as tetrabutylammonium fluoride. Silicon-based initiators such as for example 9-trimethylsilylcarbazole are preferred.

SUMMARY OF THE INVENTION

An aspect of the invention is to provide polymerization initiators which can be activated by light and which result in a high through-curing depth of the material to be cured. The initiators are to be effective at low concentration and make possible a rapid curing of the material to be cured. Moreover they are not to lead to discolorations of the material.

DETAILED DESCRIPTION OF VARIOUS EMBODIMENTS

According to the invention compositions with at least one polymerizable binder contain at least one acylgermanium compound according to general Formula (I),

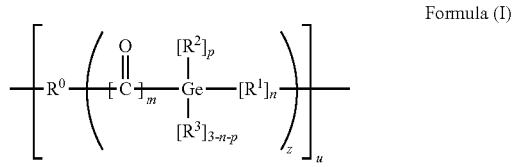

Formula (I)

in which according to a first alternative u is 1 and the two y1-positions at $R^0$ and $R^1$ are dispensed with, z is an integer of 2 to 10, wherein $R^0$ is a z-valent branched or preferably linear aliphatic, aromatic or aliphatic-aromatic hydrocarbon radical with 1 to 50, preferably 1 to 20 carbon atoms and 0 to 10, preferably 0 to 6 hetero atoms, preferably O, S, N, Si, particularly preferably O and/or S, which is substituted z times by the group in round brackets, wherein if z=2 or 3 $R^0$ can also be N or NH, N—$C_{1-3}$-alkyl or N-phenyl, and wherein if z=2 and m=0 $R^0$ can also be dispensed with, with the result that two of the groups in round brackets are connected to each other by a chemical bond between the germanium atoms, and wherein the radical $R^0$ can be substituted by one or more oxygen atoms (=O), CN, halogen, one or more branched or linear $C_{1-6}$ alkyl radicals, —O—$C_{1-6}$-alkyl radicals and/or polymerizable groups;

3

$R^1$, $R^2$ independently of each other are

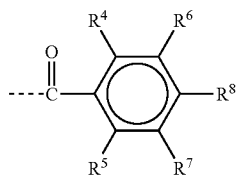

or H or have one of the meanings given for $R^3$; wherein
$R^4$, $R^5$ independently of each other are in each case H, halogen, a branched or linear $C_{1-6}$ alkyl or $-O-C_{1-6}$-alkyl radical which can be interrupted by one or more oxygen atoms;
$R^6$, $R^7$, $R^8$ independently of each other are in each case H, halogen, a branched, cyclic or preferably linear $C_{1-20}$ alkyl, -alkenyl, -alkyloxy or -alkenoxy radical, which can be interrupted by one or more O, S or $-NR^{20}-$ and can be substituted by one or more polymerizable groups and/or radicals $R^9$, wherein $R^9$ is $-OH$, $-C_xF_{2x+1}$ with x=1 to 20, $-[Si(CH_3)_2]_y-CH_3$ with y=1 to 20, and $R^{20}$ is H, halogen, a branched, cyclic or preferably linear $C_{1-20}$ alkyl, -alkenyl, -alkyloxy or -alkenoxy radical, and
wherein $R^2$ can also be a linear or branched aliphatic, aromatic or aliphatic-aromatic hydrocarbon radical with 1 to 50, preferably 1 to 20 carbon atoms and 0 to 10, preferably 0 to 6 hetero atoms, preferably O, S, N, Si, particularly preferably O and/or S, in particular a $C_{1-20}$-alkenyl radical which forms a bridge between two germanium atoms.

Compounds of the first alternative can be represented by the following Formula (I'):

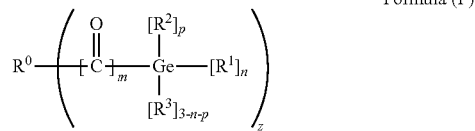

Formula (I')

The group of Formula (I') in round brackets is also referred to as the bracket term below. Compounds of Formula (I') are preferred.

According to a second alternative
u is an integer of 2 to 100 and the two y1-positions at the terminal radicals $R^0$ and $R^1$, or Ge if $R^1$ is dispensed with, are saturated by H or OH or connected to each other with formation of a chemical bond between $R^0$ and $R^1$ or Ge,
z is 1,
wherein
$R^0$ is a bivalent linear or branched aliphatic, aromatic or aliphatic-aromatic hydrocarbon radical with 1 to 50, preferably 1 to 20 carbon atoms and 0 to 10, preferably 0 to 6 hetero atoms, preferably O, S, N, Si, particularly preferably O and/or S, wherein $R^0$ can also be N—$R^{22}$ or —O—Si($R^{23}$)$_2$—O—, wherein $R^{22}$ is H, $C_{1-10}$ alkyl, preferably H or $C_{1-4}$ alkyl, or phenyl, and $R^{23}$ is $C_{1-10}$ alkyl, preferably $C_{1-4}$ alkyl or two radicals $R^{23}$ form an oxygen bridge (—O—) between two Si atoms, and wherein the radical $R^0$ can be substituted by one or more oxygen atoms (=O), CN, halogen, one or more branched or linear $C_{1-6}$ alkyl radicals, —O—$C_{1-6}$-alkyl radicals and/or polymerizable groups;

4

$R^1$ is —C(=O)— or is dispensed with,
$R^2$ is

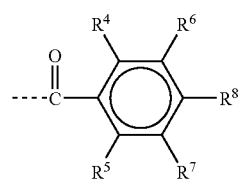

or H or has one of the meanings given for $R^3$; wherein
$R^4$, $R^5$ independently of each other are in each case H, halogen, a branched or linear $C_{1-6}$ alkyl or —O—$C_{1-6}$-alkyl radical which can be interrupted by one or more oxygen atoms;
$R^6$, $R^7$, $R^8$ independently of each other are in each case H, halogen, a branched, cyclic or preferably linear $C_{1-20}$ alkyl, -alkenyl, -alkyloxy or -alkenoxy radical, which can be interrupted by one or more O, S or —$NR^{20}$— and can be substituted by one or more polymerizable groups and/or radicals $R^9$, wherein $R^9$ is —OH, —$C_xF_{2x+1}$ with x=1 to 20, —[Si(CH_3)_2]_y—CH_3 with y=1 to 20, and $R^{20}$ is H, halogen, a branched, cyclic or preferably linear $C_{1-20}$ alkyl, -alkenyl, -alkyloxy or -alkenoxy radical.

The other variables have the following meanings in both alternatives:
m is 0 or 1,
n is 0 or 1,
p is 0 or 1,
$R^3$ is a branched or preferably linear $C_{1-18}$ alkyl radical or $C_{2-18}$ alkenyl radical, wherein these radicals can be unsubstituted or substituted one or more times by a radical which is selected from the following group:
halogen, CN,

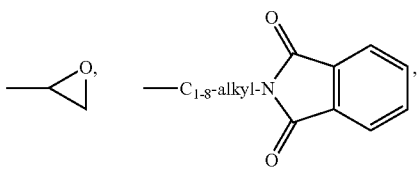

—$OR^{10}$, —$SR^{10}$, —OCO—$R^{10}$, —COO—$R^{10}$, —CH=CH—CO—$OR^{10}$, —C($C_{1-4}$ alkyl)=C($C_{1-4}$-alkyl)-CO—$OR^{10}$, —CO—$R^{13}$, —CO—CH=CH—CO—$C_{1-6}$-alkyl, —CO—CH=CH—CO-phenyl, —CO—CH=CH—COO—$C_{1-18}$-alkyl, —$NR^{11}R^{12}$, —N($R^{11}$)—CO—$R^{10}$, —N($R^{11}$)—COO—$R^{10}$, —N($R^{11}$)—CO—$NR^{11}R^{12}$, —N($R^{11}$)—CO-hal, —CO—$NR^{11}R^{12}$, —SO$_2$—$R^{10}$, —SO$_2$—$OR^{10}$, —SO$_2$—$NR^{11}R^{12}$, —PO(O$C_{1-8}$-alkyl)$_2$, —Si$R^{14}R^{15}R^{16}$, —CH=CH-phenyl, —C($C_{1-4}$-alkyl)=C($C_{1-4}$-alkyl)phenyl, phenyl-$C_{1-4}$-alkyl, phenyl, naphthyl, biphenyl, $C_{5-12}$ cycloalkyl, a saturated or unsaturated 5- or 6-membered O—, S— or N-containing heterocyclic ring, benzophenonyl, thisanthonyl, wherein
$R^{10}$ is H, $C_{1-18}$ alkyl, $C_{1-18}$ alkyl which is interrupted by one or more oxygen atoms; $C_{2-18}$ alkenyl; $C_{2-18}$ alkenyl, which is interrupted by one or more oxygen atoms; $C_{3-12}$ cycloalkyl; tetrahydropyran-2-yl, phenyl-$C_{1-20}$-alkylene; phenyl-$C_{1-20}$-alkenylene; $C_{1-6}$ alkyl which can be unsubstituted or substituted by halogen, cyclohexyl, cyclopentyl, tetrahydrofuranyl, furanyl or isopropyl-4-methyl-cyclohexyl, is phenyl, naphthyl or biphenyl, wherein these ring systems can be unsubstituted or substituted by 1 to 5 halogen atoms; $C_{1-8}$ alkyl; $C_{1-8}$ alkoxy and/or $C_{1-8}$ alkylthio radicals;

$R^{11}$, $R^{12}$ independently of each other are H; $C_{1-18}$ alkyl, $C_{1-18}$ alkyl which is interrupted by one or more oxygen atoms; $C_{2-18}$ alkenyl, $C_{2-18}$ alkenyl which is interrupted by one or more oxygen atoms; $C_{3-12}$ cycloalkyl, phenyl-$C_{1-4}$-alkyl; phenyl; naphthyl or pyridyl; wherein these ring systems can be unsubstituted or substituted by 1 to 5 halogen atoms, $C_{1-8}$ alkyl, $C_{1-8}$ alkoxy and/or $C_{1-8}$ alkylthio radicals; or $R^{11}$ and $R^{12}$ together form a 5- or 6-membered O—, S— or N-containing heterocyclic ring which for its part can be anellated with an aliphatic or aromatic ring, $R^{13}$ is $C_{1-18}$ alkyl, $C_{2-18}$ alkenyl which is interrupted by one or more O atoms, $C_{3-12}$ cycloalkyl, phenyl-$C_{1-4}$ alkyl, phenyl, naphthyl or biphenyl, wherein the named ring systems can be unsubstituted or substituted by 1 to 5 $C_{1-8}$ alkyl, $C_{1-8}$ alkoxy, $C_{1-8}$ alkylthio radicals and/or halogen atoms;

$R^{14}$, $R^{15}$, $R^{16}$ independently of each other are in each case H, $C_{1-8}$ alkyl, $C_{2-8}$ alkenyl, $C_{7-9}$ phenylalkyl, —O—$C_{1-8}$-alkyl, phenyl or —O—Si$R^{17}R^{18}R^{19}$, wherein $R^{17}$, $R^{18}$, $R^{19}$ independently of each other are in each case H, $C_{1-8}$ alkyl, $C_{2-8}$ alkenyl, $C_{7-9}$ phenylalkyl, —O—$C_{1-8}$ alkyl or phenyl, or $R^3$ is a branched or preferably linear $C_{2-18}$ alkyl radical or a $C_{2-18}$ alkylene radical which is interrupted one or more times by —O—, —NH—, —N$R^{11}$—, —S—, wherein the radicals can be unsubstituted or substituted one or more times by a radical which is chosen from the following group:

halogen, CN, —O$R^{10}$, —S$R^{10}$, —OCO—$R^{10}$, —COO—$R^{10}$, —N$R^{11}R^{12}$, —N($R^{11}$)—CO—$R^{10}$, —N($R^{11}$)—COO—$R^{10}$, —N($R^{11}$)—CO—N$R^{11}R^{12}$, —N($R^{11}$)—CO-hal, —CO—N$R^{11}R^{12}$, —SO$_2$—$R^{10}$, —SO$_2$—O$R^{10}$, —SO$_2$—N$R^{11}R^{12}$, —PO(O$C_{1-18}$-alkyl)$_2$, —Si$R^{14}R^{15}R^{16}$, phenyl-$C_{1-4}$-alkyl, phenyl, $C_{5-12}$ cycloalkyl;

wherein $R^{10}$, $R^{11}$, $R^{12}$, $R^{14}$, $R^{15}$ and $R^{16}$ are as defined above;

or $R^3$ is a branched or preferably linear $C_{2-18}$ alkyl radical or a $C_{2-18}$ alkylene radical, which is interrupted one or more times by —CO—, —COO—, —OCO—, —OCOO—, —CO—N($R^{11}$)—, —N($R^{11}$)—CO—, —N($R^{11}$)—CO—N($R^{11}$)—, —N($R^{11}$)—COO—, —COO—$C_{1-6}$-alkylene, —COS—$C_{1-18}$-alkylene, —SO$_2$—, —SO$_2$—O—, —SO$_2$—N($R^{11}$)—, —(CH$_3$)$_2$Si[OSi(CH$_3$)$_2$]$_q$—, with q=1 to 6; phenyl-$C_{1-4}$-alkylene, phenylene, naphthylene, biphenylene, $C_{5-12}$ cycloalkylene or a 5- or 6-membered O—, S— or N-containing heterocyclic ring;

wherein $R^{11}$ is as defined above;

or $R^3$ is trimethylsilyl, hal-(CH$_3$)$_2$Si—[OSi(CH$_3$)$_2$]$_r$—, (CH$_3$)$_3$Si—[OSi(CH$_3$)$_2$]$_r$— with r=1 to 6, —COOH, —COO—$R^{10}$, —CO—N$R^{11}R^{12}$, —CO-vinyl, —CO-phenyl, wherein the phenyl radical can be unsubstituted or substituted by —CH$_3$, —OCH$_3$ and/or —Cl;

wherein $R^{10}$, $R^{11}$ and $R^{12}$ are as defined above;

or $R^3$ is phenyl-$C_{1-20}$-alkyl, phenyl, naphthyl or biphenyl, $C_{5-12}$ cycloalkyl or a saturated or unsaturated 5- or 6-membered O—, S— or N-containing heterocyclic ring, wherein these ring systems can be unsubstituted or substituted by 1 to 5 halogen atoms, $C_{1-8}$ alkyl, $C_{1-8}$ alkoxy, $C_{1-8}$ alkylthio radicals and/or —N$R^{11}R^{12}$, wherein $R^{11}$ and $R^{12}$ are as defined above.

Preferably $R^3$ is halogen, OH, an aromatic $C_{6-30}$ radical which can be substituted by a branched, cyclic or preferably linear $C_{1-20}$ alkyl, -alkenyl, -alkoxy or -alkenoxy radical, wherein the named radicals can be interrupted by one or more O, S or N atoms and/or can be substituted by one or more polymerizable groups and/or radicals $R^9$, or is a branched, cyclic or preferably linear $C_{1-20}$ alkyl, -alkenyl, -alkoxy or -alkenoxy radical which can be interrupted one or more times by O, S or —N$R^{20}$— and can be substituted by one or more polymerizable groups and/or radicals $R^9$, wherein $R^9$ is —OH, —$C_xF_{2x+1}$ with x=1 to 20, —[Si(CH$_3$)$_2$]$_y$—CH$_3$ with y=1 to 20, and $R^{20}$ is H, halogen, a branched, cyclic or preferably linear $C_{1-20}$ alkyl, -alkenyl, -alkyloxy or -alkenoxy radical.

Additionally, two of the radicals $R^1$, $R^2$ or $R^3$ from Formula (I) or (I') can be connected to each other to form a 5- to 8-membered ring which for its part can be anellated with one or more, preferably 1 or 2 aliphatic or aromatic rings. These rings can contain further hetero atoms in addition to the germanium atom, preferably O, S or N atoms. The number of additional hetero atoms is preferably 1 or 2. Different radicals, or in the case of m, n, p or 3-n-p>1 also identical radicals, can be connected to each other to form one or more rings. For example in the case where p=2 the two radicals $R^2$ can be connected to each other. By the connection of the radicals cyclic germanium compounds are formed, i.e. compounds in which the germanium atom is integrated into a ring. If two times two groups are linked to each other then these are spiro compounds with germanium as central atom (spiro atom). The formed rings can be unsubstituted or substituted one or more times, preferably once or twice. Preferred substituents are $C_{1-4}$ alkyl groups or =O.

The variables of Formulae (I) and in particular (I') preferably have the following meanings:

$R^0$ a saturated aliphatic hydrocarbon radical with 1 to 18, preferably 1 to 6 carbon atoms, an aromatic hydrocarbon radical with 6 to 10, preferably 6 carbon atoms, an aliphatic-aromatic hydrocarbon radical with 7 to 24 carbon atoms, wherein in these radicals 1 to z non-adjacent carbon atoms can be replaced by oxygen, $R^1$, $R^2$ independently of each other are

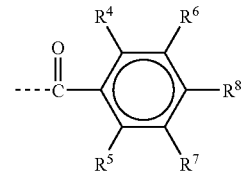

or H or have one of the meanings given for $R^3$; wherein $R^4$, $R^5$ independently of each other are in each case H, halogen, a branched or linear $C_{1-6}$ alkyl or —O—$C_{1-6}$-alkyl radical;

$R^6$, $R^7$, $R^8$ independently of each other are in each case H, halogen, a branched, cyclic or preferably linear $C_{1-20}$ alkyl, -alkenyl, -alkyloxy or -alkenoxy radical, which can be interrupted by one or more O, S or —NR'— and can be substituted by one or more polymerizable groups and/or radicals $R^9$, wherein R' is H, halogen, a branched, cyclic or preferably linear $C_{1-20}$ alkyl, -alkenyl, -alkyloxy or -alkenoxy radical;

$R^3$ is a branched or preferably linear $C_{1-18}$ alkyl radical or $C_{2-18}$ alkenyl radical, wherein these radicals can be unsubstituted or substituted one or more times by a radical which is selected from the following group:
halogen, CN,

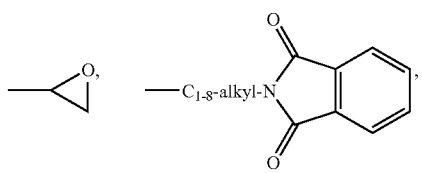

—OR$^{10}$, —SR$^{10}$, —OCO—R$^{10}$, —COO—R$^{10}$, —CH=CH—CO—OR$^{10}$, —C(C$_{1-4}$-alkyl)=C(C$_{1-4}$-alkyl)-CO—OR$^{10}$, —CO—R$^{13}$, —CO—CH=CH—CO—C$_{1-6}$-alkyl, —CO—CH=CH—CO-phenyl, —CO—CH=CH—COO—C$_{1-18}$-alkyl, —NR$^{11}$R$^{12}$, —N(R$^{11}$)—CO—R$^{10}$, —N(R$^{11}$)—COO—R$^{10}$, —N(R$^{11}$)—CO—NR$^{11}$R$^{12}$, —N(R$^{11}$)—CO-hal, —CO—NR$^{11}$R$^{12}$, —SO$_2$—R$^{10}$, —SO$_2$—OR$^{10}$, —SO$_2$—NR$^{11}$R$^{12}$, —PO(OC$_{1-8}$-alkyl)$_2$, —SiR$^{14}$R$^{15}$R$^{16}$, —CH=CH-phenyl, —C(C$_{1-4}$-alkyl)=C(C$_{1-4}$-alkyl)phenyl, phenyl-C$_{1-4}$-alkyl, phenyl, naphthyl, biphenyl, C$_{5-12}$ cycloalkyl, a 5 or 6-membered O—, S— or N-containing heterocyclic ring, benzophenonyl, thisanthonyl, wherein R$^{10}$ is H, C$_{1-18}$ alkyl, C$_{2-18}$ alkenyl; C$_{2-18}$ alkenyl which is interrupted by one or more oxygen atoms; C$_{3-12}$ cycloalkyl; tetrahydropyran-2-yl, phenyl-C$_{1-4}$-alkylene; phenyl-C$_{1-4}$-alkenylene; C$_{1-6}$ alkyl which can be unsubstituted or substituted by halogen, cyclohexyl, cyclopentyl, tetrahydrofuranyl, furanyl or isopropyl-4-methyl-cyclohexyl; is phenyl, naphthyl or biphenyl; wherein these ring systems can be unsubstituted or substituted by 1 to 5 halogen atoms; C$_{1-8}$ alkyl; C$_{1-8}$ alkoxy and/or C$_{1-8}$ alkylthio radicals;

R$^{11}$, R$^{12}$ independently of each other are H; C$_{1-18}$ alkyl, C$_{2-18}$ alkenyl, C$_{2-18}$ alkenyl which is interrupted by one or more oxygen atoms, C$_{3-12}$ cycloalkyl, phenyl-C$_{1-4}$-alkyl; phenyl, naphthyl or pyridyl; wherein these ring systems can be unsubstituted or substituted by 1 to 5 halogen atoms, C$_{1-8}$ alkyl, C$_{1-8}$ alkoxy and/or C$_{1-8}$ alkylthio radicals; or R$^{11}$ and R$^{12}$ together form a 5 or 6-membered O—, S— or N-containing heterocyclic ring which for its part can be anellated with an aliphatic or aromatic ring, R$^{13}$ is C$_{1-18}$ alkyl, C$_{2-18}$ alkenyl which is interrupted by one or more O atoms, C$_{3-12}$ cycloalkyl, phenyl-C$_{1-4}$ alkyl, phenyl, naphthyl or biphenyl, wherein the named ring systems can be unsubstituted or substituted by 1 to 5 C$_{1-8}$ alkyl, C$_{1-8}$ alkoxy, C$_{1-8}$ alkylthio radicals and/or halogen atoms;

R$^{14}$, R$^{15}$, R$^{16}$ independently of each other are in each case H, C$_{1-8}$ alkyl, C$_{2-8}$ alkenyl, C$_{7-9}$ phenylalkyl, —O—C$_{1-8}$-alkyl, phenyl or —O—SiR$^{17}$R$^{18}$R$^{19}$, wherein R$^{17}$, R$^{18}$, R$^{19}$ independently of each other are in each case H, C$_{1-8}$ alkyl, C$_{2-8}$ alkenyl, C$_{7-9}$ phenylalkyl, —O—C$_{1-8}$ alkyl or phenyl, and wherein R$^{10}$, R$^{11}$ and R$^{12}$ are as defined above;
or
R$^3$ is a branched or preferably linear C$_{2-18}$ alkyl radical or a C$_{2-18}$ alkylene radical which is interrupted one or more times by —O—, —NH—, —NR$^{11}$—, —S—, wherein the radicals can be unsubstituted or substituted one or more times by a radical which is chosen from the following group:

halogen, CN, —OR$^{10}$, —SR$^{10}$, —OCO—R$^{10}$, —COO—R$^{10}$, —NR$^{11}$R$^{12}$, —N(R$^{11}$)—CO—R$^{10}$, —N(R$^{11}$)—COO—R$^{10}$, —N(R$^{11}$)—CO—NR$^{11}$R$^{12}$, —N(R$^{11}$)—CO-hal, —CO—NR$^{11}$R$^{12}$, —SO$_2$—R$^{10}$, —SO$_2$—OR$^{10}$, —SO$_2$—NR$^{11}$R$^{12}$, —PO(OC$_{1-8}$-alkyl)$_2$, —SiR$^{14}$R$^{15}$R$^{16}$, phenyl-C$_{1-4}$-alkyl, phenyl, C$_{5-12}$ cycloalkyl;

wherein R$^{10}$, R$^{11}$, R$^{12}$, R$^{14}$, R$^{15}$ and R$^{16}$ are as defined above;

or

R$^3$ is a branched or preferably linear C$_{2-18}$ alkyl radical or a C$_{2-18}$ alkylene radical, which is interrupted one or more times by —CO—, —COO—, —OCO—, —OCOO—, —CO—N(R$^{12}$)—, —N(R$^{12}$)—CO—, —N(R$^{12}$)—CO—N(R$^{12}$)—, —N(R$^{12}$)—COO—, —COO—C$_{1-6}$-alkylene, —COS—C$_{1-18}$-alkylene, —SO$_2$—, —SO$_2$—O—, —SO$_2$—N(R$^{12}$)—, —(CH$_3$)$_2$Si[OSi(CH$_3$)$_2$]$_q$—, with q=1 to 6; phenyl-C$_{1-4}$-alkylene, phenylene, naphthylene, biphenylene, C$_{5-12}$ cycloalkylene or a 5 or 6-membered O—, S— or N-containing heterocyclic ring;

wherein R$^{12}$ is as defined above;
or
R$^3$ is trimethylsilyl, hal-(CH$_3$)$_2$Si—[OSi(CH$_3$)$_2$]$_r$—, (CH$_3$)$_3$Si—[OSi(CH$_3$)$_2$]$_r$— with r=1 to 6, —COOH, —COO—R$^{10}$, —CO—NR$^{11}$R$^{12}$, —CO-vinyl, —CO-phenyl, wherein the phenyl radical can be unsubstituted or substituted by —CH$_3$, —OCH$_3$ and/or —Cl;

wherein R$^{10}$, R$^{11}$ and R$^{12}$ are as defined above;
or
R$^3$ is phenyl-C$_{1-4}$-alkyl, phenyl, naphthyl or biphenyl, C$_{5-12}$ cycloalkyl or a 5 or 6-membered O—, S— or N-containing heterocyclic ring, wherein these ring systems can be unsubstituted or substituted by 1 to 5 halogen atoms, C$_{1-8}$ alkyl, C$_{1-8}$ alkoxy, C$_{1-8}$ alkylthio radicals and/or —NR$^{11}$R$^{12}$, wherein R$^{11}$ and R$^{12}$ are as defined above and
m is 0 or 1,
n is 0 or 1,
p is 0 or 1,
z is 2 to 10, preferably 2 to 6 and in particular 2, 3 or 4.

According to a particularly preferred embodiment, R$^3$ of Formulae (I) and (I') has the following meaning:

R$^3$ is an aromatic C$_{6-10}$ radical which can be substituted by a branched or preferably linear C$_{1-18}$ alkyl, -alkenyl, -alkoxy or -alkenoxy radical, wherein the named radicals can be interrupted by one or more O atoms, or is a branched or preferably linear C$_{1-18}$ alkyl, -alkenyl, -alkoxy or -alkenoxy radical which can be interrupted one or more times by O.

According to a quite particularly preferred embodiment, R$^3$ is C$_{1-4}$, in particular C$_1$, C$_2$ and/or C$_3$ alkyl.

In the case of Formula (I'), alkyl groups with 1 to 6 carbon atoms are particularly preferred as radical R$^0$, wherein z hydrogen atoms of these groups are substituted by the bracket term of Formula (I'). Linear alkyl groups are particularly preferred. Preferred aromatic hydrocarbon radicals are benzene radicals which are substituted z times by the bracket term. Preferred aliphatic-aromatic hydrocarbon radicals are obtained by combining the preferred aliphatic and aromatic groups. Combinations of two or more benzene rings, preferably 2 to 3 benzene rings and an aliphatic group, may be named in particular. The bonding with the bracket term preferably takes place via benzene radicals. The named radicals can contain one or more oxygen atoms, wherein aliphatic carbon atoms are preferably replaced by oxygen atoms. The germanium compounds according to the invention of Formula (I') are preferably constructed symmetrical, with the result that the number of oxygen atoms or other hetero atoms preferably corresponds to the number of groups in round brackets, i.e. z or a multiple thereof, preferably z.

According to one embodiment of the invention, accordingly compositions are preferred which contain at least one compound of Formula (I'),

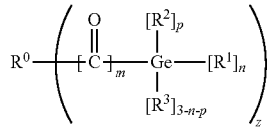

Formula (I')

in which
R⁰ is an alkyl group with 1 to 6 carbon atoms, wherein z hydrogen atoms of this group are substituted by the bracket term of Formula (I'),
$R^1$, $R^2$ independently of each other are

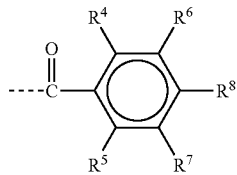

or H or have one of the meanings given for $R^3$; wherein
$R^4$, $R^5$ independently of each other are in each case H, halogen, a branched or linear $C_{1-6}$ alkyl or —O—$C_{1-6}$-alkyl radical;
$R^6$, $R^7$, $R^8$ independently of each other are in each case H, halogen, a branched, cyclic or preferably linear $C_{1-20}$ alkyl, -alkenyl, -alkyloxy or -alkenoxy radical, which can be interrupted by one or more O, S or —NR'— and can be substituted by one or more polymerizable groups and/or radicals $R^9$, wherein R' is H, halogen, a branched, cyclic or preferably linear $C_{1-20}$ alkyl, -alkenyl, -alkyloxy or -alkenoxy radical;
$R^3$ is an aromatic $C_{6-10}$ radical which can be substituted by a branched or preferably linear $C_{1-18}$ alkyl, -alkenyl, -alkoxy or -alkenoxy radical, wherein the named radicals can be interrupted by one or more O atoms, or is a branched or preferably linear $C_{1-18}$ alkyl, -alkenyl, -alkoxy or -alkenoxy radical which can be interrupted one or more times by O,
m is 0 or 1,
n is 0 or 1,
p is 0 or 1,
z is 2 to 6.

Compounds of Formula (I) particularly preferred according to the invention can be represented by the following Formula (II):

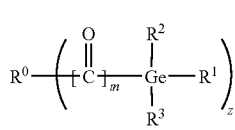

Formula (II)

in which
$R^1$, $R^2$, $R^3$ independently of one another are

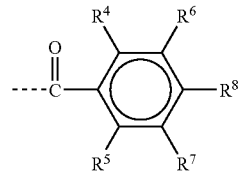

a $C_{1-3}$ alkyl radical or a $C_{1-3}$ acyl group such as e.g. an acetyl group;
$R^4$, $R^5$ independently of each other are in each case H, halogen, a branched or linear $C_{1-6}$ alkyl or —O—$C_{1-6}$ alkyl radical;
$R^6$, $R^7$, $R^8$ independently of each other are in each case H, halogen, a branched, cyclic or preferably linear $C_{1-20}$ alkyl, -alkenyl, -alkyloxy or -alkenoxy radical which is interrupted one or more times by O, S or —$NR^{20}$— and can be substituted by one or more polymerizable groups and/or radicals $R^9$; wherein
$R^9$ is —OH, —$C_xF_{2x+1}$ with x=1 to 20, —$[Si(CH_3)_2]_y$—$CH_3$ with y=1 to 20, and
$R^{20}$ is H, halogen, a branched, cyclic or preferably linear $C_{1-20}$ alkyl, -alkenyl, -alkyloxy or -alkenoxy radical and
m has the meaning given above.

Further preferred are germanium compounds according to the following Formula (III)

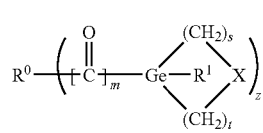

Formula (III)

in which
$R^1$ is

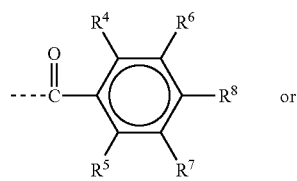

a $C_{1-3}$ alkyl radical or a $C_{1-3}$ acyl group such as e.g. an acetyl group;
s, t independently of each other are an integer from 0 to 6, preferably 1 to 3, wherein s and t are chosen such that the sum of the ring atoms including the germanium atom is 5 to 8, and
X is N—$R^{21}$, O, S or is absent, wherein $R^{21}$ is H or $C_{1-10}$ alkyl, preferably H or $C_{1-4}$ alkyl and
$R^0$ and m have the meanings given above.

The germanium-containing ring can be anellated with one or more, preferably 1 or 2 aliphatic or aromatic rings and be unsubstituted or substituted one or more times, preferably once or twice, whereby the number of hydrogen atoms of the ring is correspondingly reduced. Preferred substituents are $C_{1-4}$ alkyl groups or =O. Preferred are compounds of the Formula (III) in which the germanium-containing ring is not anellated with further rings and is unsubstituted apart from $R^{21}$.

Further preferred are germanium compounds according to the following Formulae (IV) and (V)

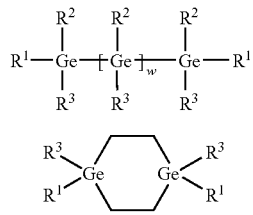
Formula IV

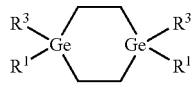
Formula V in which $R^1$, $R^2$ and $R^3$ have the meanings given above and w is an integer from 0 to 6, preferably 0 to 4 and in particular 0.

Also preferred are germanium compounds according to the following Formula (VI):

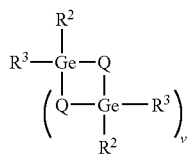
Formula VI in which
$R^2$, $R^3$ independently of each other are

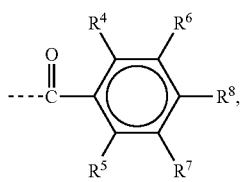

a $C_{1-3}$ alkyl radical or a $C_{1-3}$ acyl group such as e.g. an acetyl group;
v is an integer from 1 to 3, preferably 1 to 2, and
Q is $N-R^{22}$, O, S, $-CH_2-$, $-CH=CH-$, $-CH_2-CH_2-$ or $-O-Si(R^{23})_2-O-$, wherein $R^{22}$ is H, $C_{1-10}$ alkyl, preferably H or $C_{1-4}$ alkyl, or phenyl, and $R^{23}$ is $C_{1-10}$ alkyl, preferably $C_{1-4}$ alkyl or two radicals $R^{23}$ form an oxygen bridge ($-O-$) between two Si atoms.

In all acylgermanium compounds according to the invention of the above Formulae, in each case 1 to 3 acyl groups are bonded to each germanium atom, wherein germanium compounds with 1 or 2 acyl groups per germanium atom are preferred. The acylgermanium compounds according to the invention are thus characterized in that they contain at least two germanium atoms each of which has at least one acyl group.

All stereoisomeric forms and mixtures of various stereoisomeric forms such as e.g. racemates are covered by Formula (I) and the other formulae shown here. The formulae cover only those compounds that conform to the chemical valence theory.

The indication that a radical can be interrupted by a hetero atom such as O is to be understood to mean that the O atoms are inserted into the carbon chain of the radical, i.e. are bordered on both sides by carbon atoms. The number of hetero atoms is therefore smaller than the number of carbon atoms by at least 1 and the hetero atoms cannot be terminal.

In the case of hydrocarbon radicals which contain carbon and hetero atoms, the number of hetero atoms, not counting substituents, is always less than the number of carbon atoms.

Halogen (abbreviated to hal) preferably stands for F, Cl, Br or I, in particular F, Cl, quite particularly preferably Cl.

Alkyl, even if it is not expressly indicated, stands for linear and branched groups, wherein linear alkyl radicals are preferred in all cases.

Preferred polymerizable groups which can be present as substituents in the above radicals are vinyl, styryl, (meth)acrylate, (meth)acrylamide and/or N-alkylacrylamide, particularly preferably (meth)acrylate, (meth)acrylamide and/or N-alkylacrylamide. The radicals $R^2$, $R^3$, $R^6$, $R^7$ and $R^8$ are preferably substituted with 0 to 3, in particular 0 to 1 polymerizable groups. The polymerizable groups are preferably arranged terminal.

According to the invention those compounds of general Formulae (I'), (II) and (IV) are preferred in which the variables have the following meanings which can be chosen independently of each other:
$R^1$

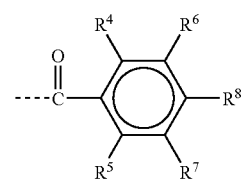

or H, or one of the meanings given for $R^2$ and $R^3$;
$R^2$, $R^3$ independently of each other a linear $C_{1-4}$ alkyl or -alkenyl radical which can be substituted by one or more polymerizable groups, or a $C_{1-3}$ acyl group such as e.g. an acetyl group;
$R^4$, $R^5$ independently of each other in each case H, halogen, a branched or linear $C_{1-4}$ alkyl or $-O-C_{1-4}$ alkyl radical, in particular H;
$R^6$, $R^7$, $R^8$ independently of each other in each case H, halogen, a linear $C_{1-20}$ alkyl, -alkenyl, -alkoxy or -alkenoxy radical which can be interrupted by one or more $-O-$, $-S-$ or $-NR^{20}-$ radicals and substituted by one or more polymerizable groups, in particular H; and
wherein the other variables have the meanings given above.

Particularly preferred definitions of the variables of general Formulae (I'), (II) and (IV) which likewise can be chosen independently of each other are:
$R^1$

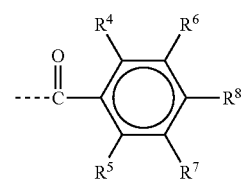

or one of the meanings given for $R^2$ and $R^3$;
$R^2$, $R^3$ $C_1$-$C_4$ alkyl;
$R^4$, $R^5$, $R^8$ H, Cl, $CH_3$, $OCH_3$;
$R^6$, $R^7$ H, $C_1$-$C_4$ alkyl which can be interrupted by one or more O atoms, and
wherein the other variables have the meanings given above.

Quite particularly preferred are compounds of Formula (II) in which $R^4=R^5$ and/or $R^6=R^7$.

Particularly preferred are naturally those compounds in which all variables have one of the preferred and in particular the particularly preferred meanings.

Specific examples of particularly preferred compounds are:
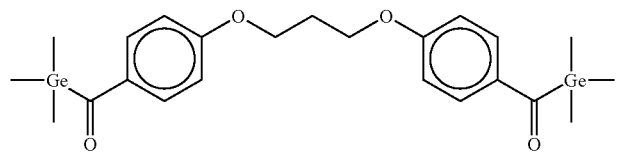
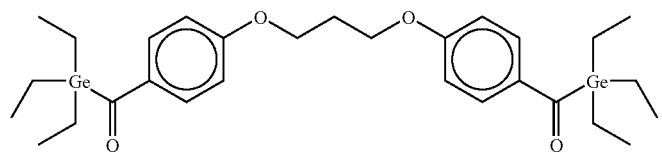
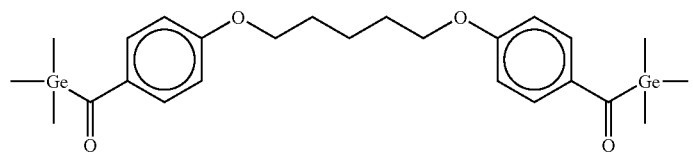
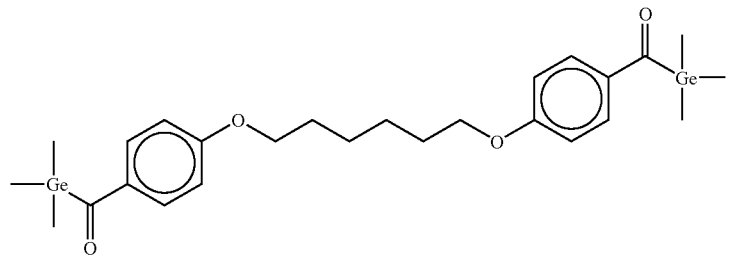
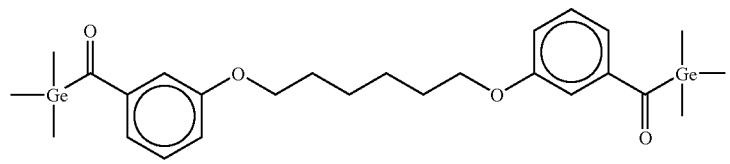
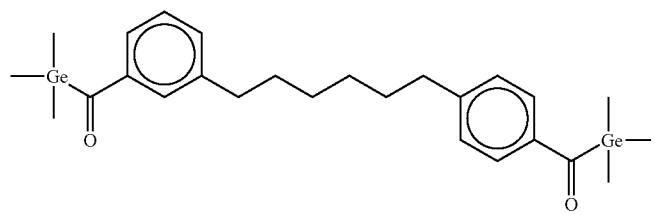
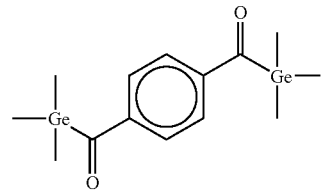
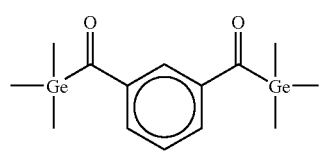
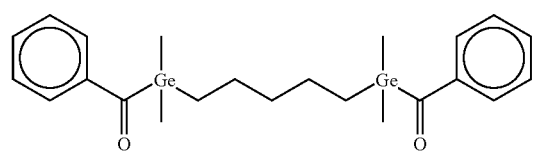
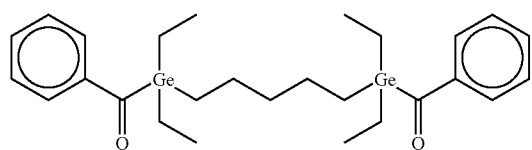
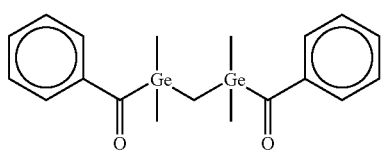
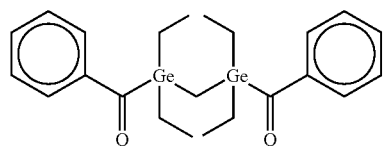
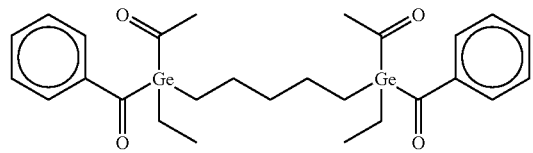

-continued
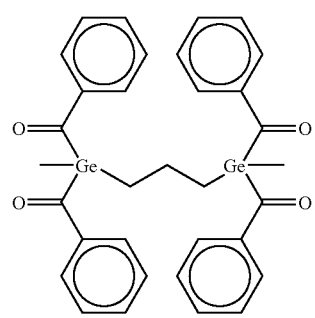
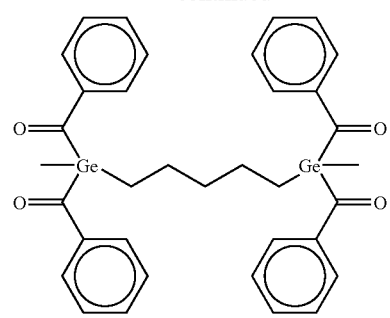
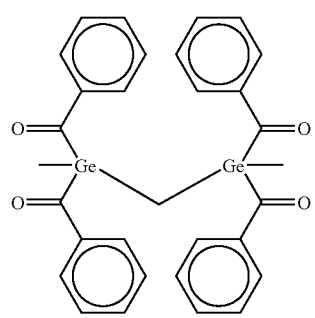
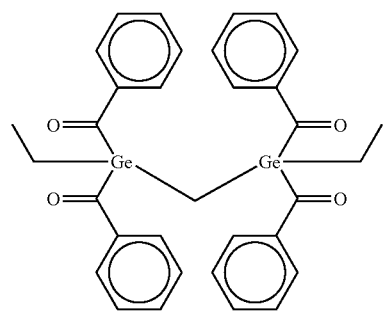
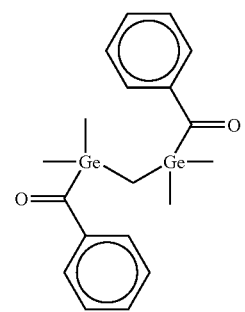
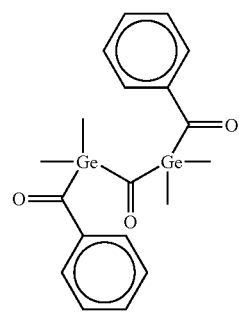
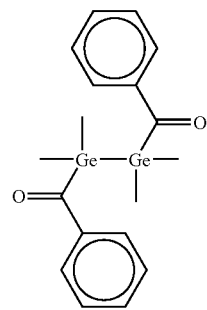
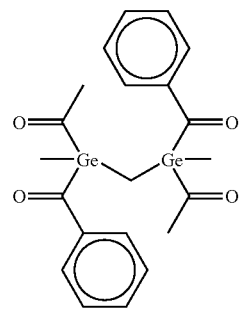
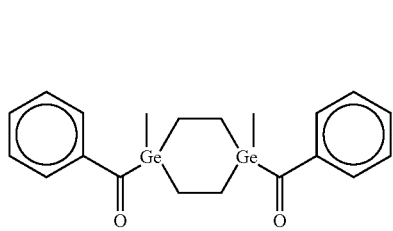
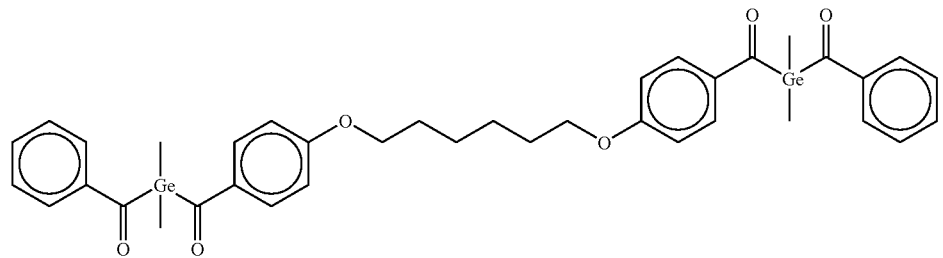
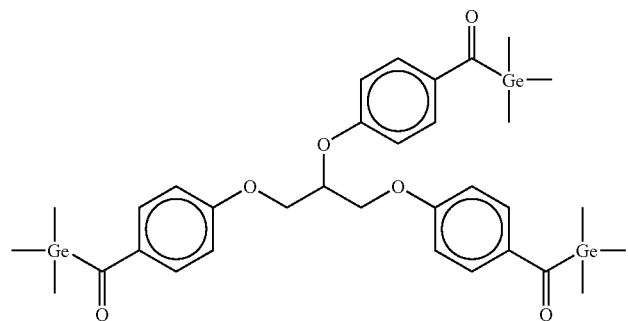

-continued
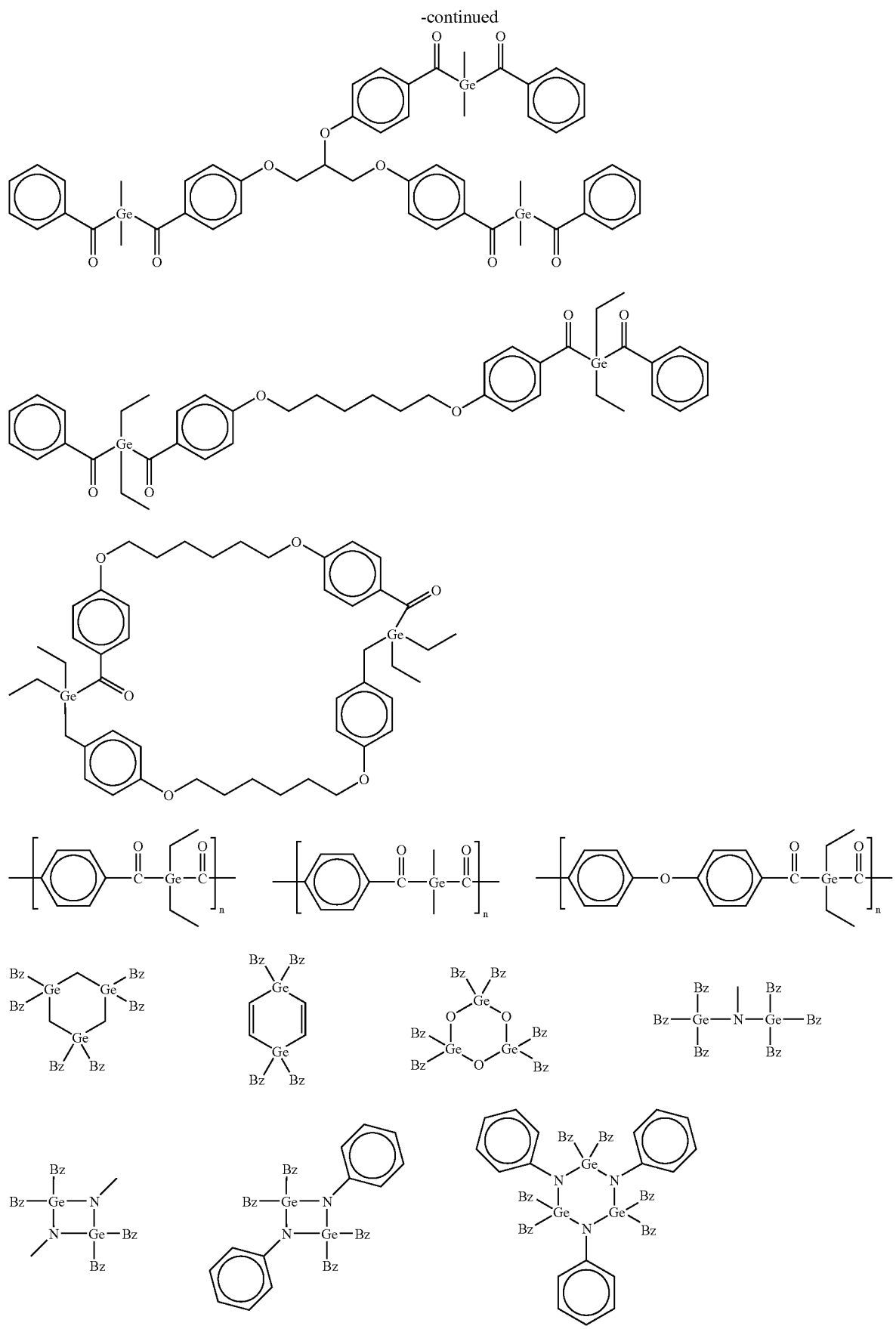

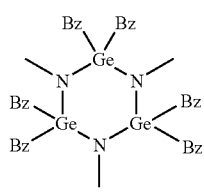 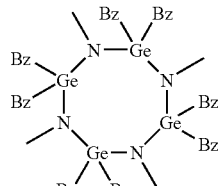 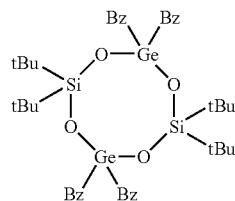

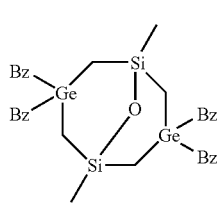 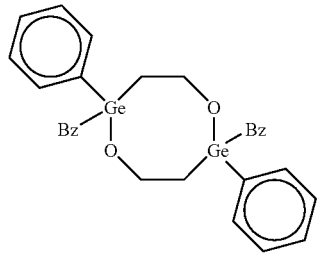

The meanings coming from the preferred compounds shown above for the variables of Formulae (I) to (VI) are generally preferred and are not restricted to the specifically shown compounds.

The compounds according to general Formula (I) with several monoacylgermanium groups can be synthesized e.g. according to a method by Yamamoto et. al. (Yamamoto, K.; Hayashi, A.; Suzuki, S.; Tsuji J.; Organometallics; 6 (1987) 974), which is hereby incorporated by reference in its entirety) by reacting hexaalkyldigermanium with acid chloride:

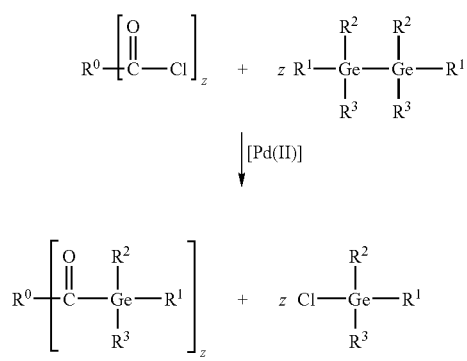

Specific Example:

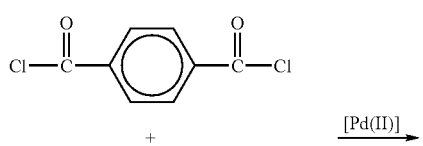

-continued

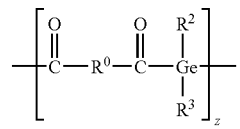

A possibility for the preparation of compounds according to general Formula (I) with several bisacylgermanium groups or of oligomeric or polymeric compounds is the reaction of the corresponding lithiated germanium compounds with acid chlorides according to Castel et. al. (Castel, A.; Riviere, P.; Satgé, J.; Ko, H. Y.; Organometallics; 9 (1990) 205), which is hereby incorporated by reference in its entirety):

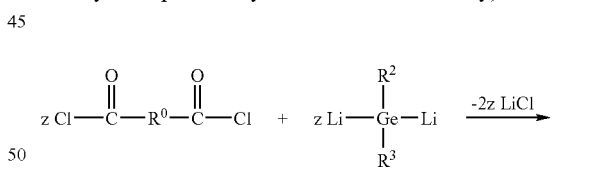

Specific Example:

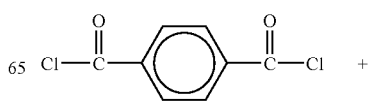

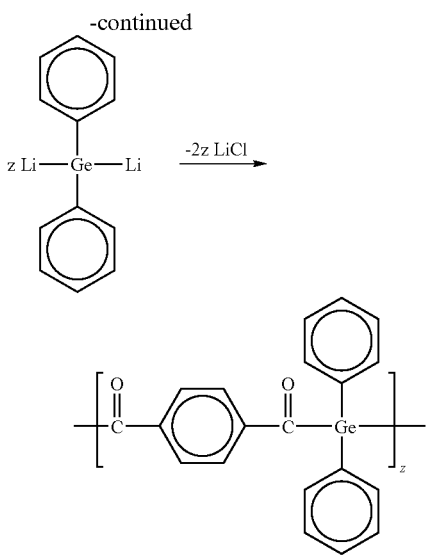

Lithiated aromatic germanium compounds can be prepared e.g. by reacting the corresponding germanium halide (X=halogen) with lithium (Li) (Nishimura, T.; Inoue-Ando, S.; Sato, Y., J. Chem. Soc., Perkin Trans. 1; (1994) 1589), which is hereby incorporated by reference in its entirety) or hydrogermanium with n-butyllithium (BuLi) (Castel, A.; Riviere, P.; Satgé, J.; Ko, H. Y.; Organometallics; 9 (1990) 205), which is hereby incorporated by reference in its entirety):

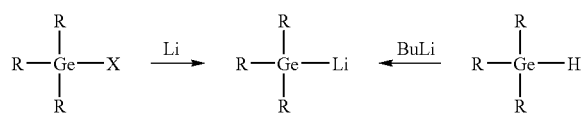

Furthermore mono- and bisacylgermanes can be synthesized by reacting a carbanion which is obtained from 1,3-dithians with germanium chlorides according to Brook et. al. (Brook, A. G.; Duff, J. M.; Jones, P. F.; Davis, N. R.; "Synthesis of Silyl and Germyl Ketones" J. Am Chem. Soc. 89(2), 431-434 (1967), which is hereby incorporated by reference in its entirety). This synthesis path is particularly suitable for the preparation of bisalkylbisacylgermanes:

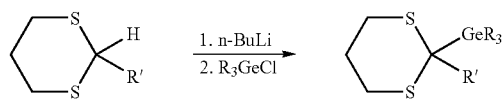

The dithianes obtained can be hydrolyzed to form the corresponding ketones according to methods which are generally known to a person skilled in the art (according to Brook, A. G.; Duff, J. M.; Jones, P. F.; Davis, N. R.; "Synthesis of Silyl and Germyl Ketones" J. Am Chem. Soc. 89(2), 431-434 (1967), which is hereby incorporated by reference in its entirety) or e.g. also according to Sharma, H. K.; Cervanes-Lee, F.; Pannel, K. H.; "Organometalloidal Derivatives of the Transition Metals, XXVII. Chemical and Structural Investigations on (ferrocenylacyl)germanes)", J. Organomet. Chem. 409, 321-330 (1991), which is hereby incorporated by reference in its entirety:

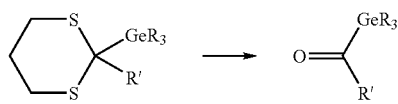

The acylgermanium compounds of general Formula (I) are particularly suitable as photoinitiators for polymerization, in particular as initiators for radical polymerization, photoaddition and for thiol-ene reaction (polyaddition). It was found with these initiators that, upon irradiation with light, a high thorough curing depth can be achieved compared with customary photoinitiators without the initiators resulting in coloured materials. This is a great advantage in many technical and particularly medical materials, such as e.g. dental materials and bone cements.

In addition the acylgermanium compounds of Formula (I) used according to the invention are characterized by a lower cytotoxicity compared with customary initiators, which is likewise a particular advantage for medical applications. The acylgermanium compounds are therefore also particularly suitable, for example, as initiators for materials for the preparation of contact lenses but also for conventional optical lenses in which a low tendency of the initiators to discoloration is of benefit.

In this connection, it is also important that the initiators of Formula (I) are characterized by an unusually high activity, with the result that the addition of lower concentrations is sufficient for curing.

The use of initiators of Formula (I) is not limited to medical applications. The great thorough curing depth upon curing with light in the visible wavelength range is also a substantial advantage in technical applications. The compositions according to the invention are particularly suitable for a plurality of uses, such as for example as printing inks or paints, varnishes, adhesives, for the preparation of printing plates, integrated circuits, photoresists, soldering masks, inks for colour printing, as materials for holographic data storage, for the preparation of nano-sized microelectromechanical elements, optical waveguides, pre-shaped parts and for the optical preparation of information carriers.

The acylgermanium compounds according to the invention can be activated with light, preferably with UV/vis light, particularly preferably with visible light (400-800 nm) and in particular with light of a wavelength of 400 to 500 nm. To initiate polymerization, the acylgermanium compounds of Formula (I) are therefore irradiated, preferably with light in the wavelength range of 200 to 750 nm, particularly preferably 200 to 550 nm, preferably 300 to 550 nm and quite particularly preferably 350 to 500 nm. They can thus be used as initiators for laser curing and laser-induced 3D curing and also for 2-photon polymerization. They are particularly suitable as initiators for pigmented systems.

It is particularly advantageous that the initiators can also be activated with LED light sources. The wavelength of LEDs depends on the lattice constant of the substrate. The quality (thermal strength, heat expansion, constancy of the interatomic distances etc.) of the substrate determines the level of the possible power of the LEDs. In intraoral use wavelengths are only permitted from approximately 380 nm so that initiators of Formula (I) which can be activated with a wavelength in the range from 380 nm and more are particularly preferred.

Combinations of LED light sources with initiators according to Formula (I) or with compositions which contain such an initiator are also a subject of the invention. Systems of LED light sources with a wavelength in the range from 400 to 550 nm, preferably 400 to 480 nm and in particular 450±20 nm and initiators or compositions matched to this, i.e. initiators with an activation wavelength in the range from 400 to 550 nm, preferably 400 to 480 nm and quite particularly preferably approx. 450±20 nm and compositions containing these, are preferred for dental use. In addition, LED light sources with a wavelength of approximately 650±30 nm or approximately 360±30 nm, together with initiators or compositions matched to this, are preferred according to the invention.

The compositions according to the invention preferably also contain, in addition to at least one acylgermanium compound of Formula (I), a polymerizable binder. Binders based on radically and/or cationically polymerizable monomers and/or prepolymers are preferred.

Mono- or multifunctional (meth)acrylates or a mixture thereof are particularly suitable as radically polymerizable binders. By monofunctional (meth)acrylic compounds are meant compounds with one, by multifunctional (meth)acrylic compounds are meant compounds with two or more, preferably 2 to 3, polymerizable groups.

Examples regarding same are methyl, ethyl, hydroxyethyl, butyl, benzyl, tetrahydrofurfuryl or isobornyl(meth)acrylate, bisphenol-A-di(meth)acrylate, bis-GMA (an addition product of methacrylic acid and bisphenol-A-diglycidylether), UDMA (an addition product of 2-hydroxyethyl methacrylate and 2,2,4-trimethylhexamethylene diisocyanate), di-, tri- or tetraethyleneglycol di(meth)acrylate, trimethylolpropane tri(meth)acrylate, pentaerythritol tetra(meth)acrylate as well as glycerol dimethacrylate, 1,4-butanediol di(meth)acrylate, 1,10-decanediol di(meth)acrylate or 1,12-dodecanediol di(meth)acrylate. Compositions which contain at least one radically polymerizable monomer with 2 or more, preferably 2 to 3 radically polymerizable groups, are particularly preferred. Multifunctional monomers have cross-linking properties.

Hydrolysis-stable monomers such as hydrolysis-stable mono(meth)acrylates, e.g. mesityl methacrylate or 2-(alkoxymethyl)acrylic acids, e.g. 2-(ethoxymethyl)acrylic acid, 2-(hydroxymethyl)acrylic acid, N-mono- or -disubstituted acrylamides, such as e.g. N-ethyl acrylamide, N,N-dimethacrylamide, N-(2-hydroxyethyl)acrylamide, N-methyl-N-(2-hydroxyethyl)acrylamide or N-monosubstituted methacrylamides, such as e.g. N-ethyl methacrylamide or N-(2-hydroxyethyl)methacrylamide and moreover N-vinylpyrrolidone or allyl ether can also be used as radically polymerizable binders. Preferred examples of hydrolysis-stable cross-linking monomers are urethanes of 2-(hydroxymethyl)acrylic acid and diisocyanates such as 2,2,4-trimethylhexamethylene diisocyanate or isophorone diisocyanate, cross-linking pyrrolidones such as e.g. 1,6-bis(3-vinyl-2-pyrrolidonyl)-hexane, or commercially available bisacrylamides such as methylene or ethylene bisacrylamide, bis(meth)acrylamides such as e.g. N,N'-diethyl-1,3-bis(acrylamido)-propane, 1,3-bis(methacrylamido)-propane, 1,4-bis(acrylamido)-butane or 1,4-bis(acryloyl)-piperazine which can be synthesized by reaction from the corresponding diamines with (meth)acrylic acid chloride. Monomers that are liquid at room temperature, which can be used as diluting monomers, are preferred.

Low-shrinkage radically ring-opening polymerizable monomers such as e.g. mono- or multifunctional vinyl cyclopropanes or bicylic cyclopropane derivatives, preferably those described in DE 196 16 183 C2 or EP 1 413 569, or cyclic allyl sulphides, preferably those described in U.S. Pat. Nos. 6,043,361 and 6,344,556, can furthermore also be used as radically polymerizable binders. These can also be used in combination with the previously mentioned di(meth)acrylate cross-linkers. Preferred ring-opening polymerizable monomers are vinyl cyclopropanes such as 1,1-di(ethoxycarbonyl)- or 1,1-di(methoxycarbonyl)-2-vinyl cyclopropane, the esters of 1-ethoxycarbonyl- or 1-methoxycarbonyl-2-vinyl cyclopropane carboxylic acid with ethyleneglycol, 1,1,1-trimethylolpropane, 1,4-cyclohexanediol or resorcin. Preferred bicyclic cyclopropane derivatives are 2-(bicyclo[3.1.0]hex-1-yl)acrylic acid methyl or ethyl esters, their disubstitution products in 3 position such as (3,3-bis(ethoxycarbonyl)bicyclo[3.1.0]hex-1-yl)acrylic acid methyl or ethyl ester. Preferred cyclic allyl sulphides are the addition products of 2-(hydroxymethyl)-6-methylene-1,4-dithiepane or 7-hydroxy-3-methylene-1,5-dithiacylooctane with 2,2,4-trimethylhexamethylene-1,6-diisocyanate or the asymmetric hexamethylene diisocyanate trimers (Desmodur® VP LS 2294 from Bayer AG).

Moreover, styrene, styrene derivatives or divinyl benzole, unsaturated polyester, polyurethane and epoxy resins and allyl compounds or radically polymerizable polysiloxanes which can be prepared from suitable methacrylic silanes such as e.g. 3-(methacryloyloxy)propyltrimethoxysilane and are described e.g. in DE 199 03 177 C2 can be used as radically polymerizable binders.

Furthermore, mixtures of the previously named monomers with radically polymerizable, acid-group-containing monomers which are also called adhesive monomers can be used as radically polymerizable binders. Preferred acid-group-containing monomers are polymerizable carboxylic acids such as maleic acid, acrylic acid, methacrylic acid, 2-(hydroxymethyl)acrylic acid, 4-(meth)acryloyloxyethyltrimellic acid anhydride, 10-methacryloyloxydecylmalonic acid, N-(2-hydroxy-3-methacryloyloxypropyl)-N-phenylglycine or 4-vinylbenzoic acid.

Radically polymerizable phosphonic acid monomers, in particular vinylphosphonic acid, 4-vinylphenylphosphonic acid, 4-vinylbenzylphosphonic acid, 2-methacryloyloxyethylphosphonic acid, 2-methacrylamidoethylphosphonic acid, 4-methacrylamido-4-methyl-pentyl-phosphonic acid, 2-[4-(dihydroxyphosphoryl)-2-oxa-butyl]-acrylic acid or 2-[2-dihydroxyphosphoryl)-ethoxymethyl]-acrylic acid ethyl or 2,4,6-trimethylphenyl ester are also suitable as adhesive monomers.

Furthermore, acidic polymerizable phosphoric acid esters, in particular 2-methacryloyloxypropyl mono- or dihydrogen phosphate, 2-methacryloyloxyethyl mono- or dihydrogen phosphate, 2-methacryloyloxyethylphenyl hydrogen phosphate, dipentaerythritol-pentamethacryloyloxyphosphate, 10-methacryloyloxydecyl-dihydrogen phosphate, dipentaerythritol-pentamethacryloyloxyphosphate, phosphoric acid mono-(1-acryloyl-piperidine-4-yl)-ester, 6-(methacrylamido)hexyl dihydrogen phosphate and 1,3-bis-(N-acryloyl-N-propyl-amino)-propane-2-yl-dihydrogen phosphate are suitable as adhesive monomers.

In addition, polymerizable sulphonic acids are suitable as adhesive monomers, in particular vinyl sulphonic acid, 4-vinylphenyl sulphonic acid or 3-(methacrylamido)propyl sulphonic acid.

Thiol-ene resins which contain mixtures of mono- or multifunctional mercapto compounds and di- or multifunctional unsaturated monomers, above all allyl or norbornene compounds, are particularly suitable as binders curable by polyaddition.

Examples of mono- or multifunctional mercapto compounds are o, m or p-dimercaptobenzene and esters of thioglycol or of 3-mercaptopropionic acid of ethylene, propylene or butylene glycol, hexanediol, glycerol, trimethylolpropane or pentaerythritol.

Examples of di- or multifunctional allyl compounds are esters of allyl alcohol with di- or tricarboxylic acids such as malonic, maleic, glutaric, succinic, adipic, sebacic, phthalic, terephthalic or gallic acid and mono- or trifunctional allyl ethers such as e.g. diallyl ether, α,ω-bis[allyloxy]alkane, resorcin or hydroquinone diallyl ether and pyrogallol triallyl ether, or other compounds such as e.g. 1,3,5-triallyl-1,3,5-triazine-2,4,6-(1H,3H,5H)-trione, tetraallylsilane or tetraallylorthosilicate.

Examples of di- or multifunctional norbornene compounds are Diels-Alder addition products of cyclopentadiene or furan with di- or multifunctional (meth)acrylates, and esters and urethanes of 5-norbornene-2-methanol or 5-norbornene-2-ol with di- or polycarboxylic acids such as e.g. malonic, maleic, glutaric, succinic, adipic, sebacic, phthalic, terephthalic or gallic acid, with di- or polyisocyanates, such as hexamethylene diisocyanate or its cyclic trimer, 2,2,4-trimethylhexamethylene diisocyanate, toluylene diisocyanate or isophorone diisocyanate.

Furthermore acylgermanium compounds of Formula (I) can be used as coinitiators or photosensitizers for the cationic polymerization of cationically polymerizable monomers. Preferred cationically polymerizable diluting or cross-linking monomers are e.g. glycidylether or cycloaliphatic epoxides, cyclic ketene acetals, vinyl ethers, spiroorthocarbonates, oxetanes or bicyclic ortho esters. Particularly preferred examples are: triethyleneglycol divinyl ether, cyclohexanedimethanol divinyl ether, 2-methylene-1,4,6-trioxaspiro[2.2]nonane, 3,9-dimethylene-1,5,7,11-tetraoxaspiro[5.5]undecane, 2-methylene-1,3-dioxepane, 2-phenyl-4-methylene-1,3-dioxolane, bisphenol-A-diglycidylether, 3,4-epoxy-cyclohexylmethyl-3,4-epoxycyclohexanecarboxylate, bis(-(3,4-epoxycyclohexylmethyl)adipate, vinylcyclohexene dioxide, 3-ethyl-3-hydroxymethyloxetane, 1,10-decanediylbis(oxymethylene) bis(3-ethyloxetane) or 3,3-(4-xylylenedioxy)-bis-(methyl-3-ethyloxetane).

Silicic acid polycondensates, which are accessible for example by hydrolytic condensation of silanes which carry cationically polymerizable groups, preferably e.g. epoxide, oxetane, spiroortho esters and/or vinyl ether groups, are also suitable as cationically polymerizable binders. Such silicic acid polycondensates are for example described in DE 41 33 494 C2 or U.S. Pat. No. 6,096,903.

In addition to acylgermanium compounds of general Formula (I), the compositions according to the invention can additionally also advantageously contain known photoinitiators (cf. J. P. Fouassier, J. F. Rabek (Ed.), Radiation Curing in Polymer Science and Technology, Vol. II, Elsevier Applied Science, London and New York 1993), which is hereby incorporated by reference in its entirety) for the UV or visible range, such as e.g.: benzoin ether, dialkyl benzil ketals, dialkoxyacetophenones, acyl or bisacyl phosphine oxides, α-diketones such as 9,10-phenanthrenequinone, diacetyl, furil, anisil, 4,4'-dichlorobenzil and 4,4'-dialkoxybenzil and camphorquinone and if necessary coinitiators such as tertiary amines e.g. dimethylaminobenzoic acid ethyl ester or methyldiethanolamine.

Moreover, in addition to the acylgermanium compounds of general Formula (I) the compositions according to the invention can additionally contain one or more cationic photoinitiators, preferably diaryliodonium or triarylsulphonium salts. Preferred diaryliodonium salts are the commercially available photoinitiators 4-octyloxy-phenyl-phenyl-iodonium hexafluoroantimonate, isopropylphenyl-methylphenyl-iodoniumtetrakis(pentafluorophenyl) borate and 4-phenylsulphanylphenyl diphenylsulphonium hexafluorophosphate. These cationic photoinitiators can be used to accelerate the curing of compositions according to the invention based on acylgermanium compounds of general Formula (I). Conversely the curing of compositions with cationic initiators can be accelerated by adding acylgermanium compounds of the Formula (I).

Furthermore the compositions according to the invention can also contain azo compounds such as 2,2'-azobis(isobutyronitrile) (AIBN) or azobis-(4-cyanovaleric acid), or peroxides such as dibenzoyl peroxide, dilauroyl peroxide, tert-butylperoctoate, tert-butylperbenzoate or di-(tert-butyl)-peroxide in addition to the acylgermanium compounds of general Formula (I) for dual curing. To accelerate initiation by means of peroxides, combinations with aromatic amines can be used. Preferred redox systems are combinations of benzoyl peroxide with amines such as N,N-dimethyl-p-toluidine, N,N-dihydroxyethyl-p-toluidine, p-dimethylaminobenzoic acid ethyl ester or structurally related systems. In addition, redox systems consisting of peroxides and reductants such as e.g. ascorbic acid, barbiturates or sulphinic acids are also suitable for dual curing. The quantity of additional initiators lies preferably in the range from 0 to 3 wt.-%.

According to the invention compositions are preferred which contain one or more fillers, preferably organic or inorganic particulate fillers. Preferred inorganic particulate fillers are amorphous spherical nanoparticulate fillers based on oxides such as pyrogenic silica or precipitated silica, $ZrO_2$ and $TiO_2$ or mixed oxides of $SiO_2$, $ZrO_2$ and/or $TiO_2$ with an average particle diameter of 10 to 200 nm, mini fillers such as quartz, glass ceramic or glass powder with an average particle size of 0.2 to 5 μm and x-ray opaque fillers such as ytterbium trifluoride, nanoparticulate tantalum(V) oxide or barium sulphate. In addition, fibrous fillers such as nanofibres, glass fibres, polyamide or carbon fibres can also be used.

The compositions according to the invention can contain colouring agents such as dyestuffs and/or pigments as further components.

Additionally, the compositions according to the invention can if necessary contain further additives and solvents, such as e.g. water, ethanol, acetone and/or ethyl acetate.

The additives are preferably selected from stabilizers, UV absorbers, slip additives, wetting agents, dispersants, adhesion promoters, matting and brightening agents, levelling agents and film-forming auxiliaries, antiskinning agents, light-protection agents, corrosion-protection agents, flame retardants, antioxidants, optical brighteners, flow improvers, thickeners and anti-foaming agents.

The initiators according to Formulae (I) and (II) are characterized by a high reactivity and can therefore be used in low concentrations (cf. Example 7). Additionally they permit the curing also of thin layers or films without the formation of an inhibition layer. The initiators according to the invention can therefore be used to prevent the formation of an inhibition layer.

The compositions according to the invention preferably contain, relative to the total mass of the composition, 0.001 to 5 wt.-%, particularly preferably 0.01 to 4 wt.-% and in particular 0.1 to 3 wt.-% acylgermanium compound of Formula (I).

The materials according to the invention thus preferably contain:
(a) 0.001 to 5 wt.-% acylgermanium compound of general Formula (I), preferably 0.01 to 4 wt.-%, particularly preferably 0.1 to 3 wt.-%, (b) 5 to 99.9 wt.-% polymerizable binder, preferably 10 to 95 wt.-%, particularly preferably 15 to 90 wt.-%, and
(c) 0 to 90 wt.-% filler, preferably 5 to 87 wt.-%, particularly preferably 10 to 85 wt.-%.

The compositions can moreover advantageously contain:
(d) 0 to 50 wt.-% additive, preferably 0.01 to 4 wt.-%, particularly preferably 0.1 to 3 wt.-%, wherein these quantity details are relative to the total mass of all the additives, and
(e) 0 to 10 wt.-%, preferably 0.01 to 5 wt.-% pigments and/or dyestuffs.

All percentages relate to the total mass of the composition if not stated otherwise.

The compositions according to the invention are particularly suitable as adhesives, coatings, varnishes, inks, cements, composites, for the preparation of pre-shaped parts or mouldings such as rods, plates, disks, optical lenses, contact lenses and in particular as dental materials, quite particularly as filling composites.

Compositions for use as dental cements preferably contain:
(a) 0.001 to 3 wt.-% acylgermanium compound of general Formula (I),
(b) 20 to 70 wt.-% polymerizable binder,
(c) 30 to 75 wt.-% filler and
(d) 0.01 to 5 wt.-% additive.

Compositions for use as dental composites preferably contain:
(a) 0.001 to 2 wt.-% acylgermanium compound of general Formula (I),
(b) 10 to 60 wt.-% polymerizable binder,
(c) 40 to 85 wt.-% filler and
(d) 0.01 to 5 wt.-% additive.

Compositions for use as dental coating materials preferably contain:
(a) 0.001 to 5 wt.-% acylgermanium compound of general Formula (I),
(b) 20 to 99.9 wt.-% polymerizable binder,
(c) 0 to 20 wt.-% nanoparticulate fillers and
(d) 0.01 to 2 wt.-% additive,
(e) 0 to 50 wt.-% solvent.

Compositions for use as printing inks preferably contain:
(a) 0.001 to 5 wt.-% acylgermanium compound of general Formula (I),
(b) 30 to 60 wt.-% polymerizable binder,
(c) 1 to 45 wt.-% colouring agent and
(d) 0.01 to 30 wt.-% additive.

Compositions for use as varnish, for example as white varnish or as varnish for optical fibres, preferably contain:
(a) 0.001 to 5 wt.-% acylgermanium compound of general Formula (I),
(b) 55 to 99.5 wt.-% polymerizable binder,
(c) 0.1 to 50 wt.-% pigment and optionally
(d) 0.01 to 30 wt.-% additive A preferred pigment for the preparation of varnishes is $TiO_2$.

Dental materials which can be cured by thiol-ene reaction preferably contain a mixture of one or more polythiol compounds and one or more polyvinyl compounds, wherein one or more of these compounds can be present in oligomeric form. Preferably, 45 to 55% of the functional groups of these mixtures are thiol groups, the remaining groups can be vinyl groups. The mixtures can furthermore contain one or more fillers, wherein the quantity of polymerizable resins preferably lies in the range from 10 to 40 wt.-% and the filler quantity preferably in the range from 60 to 90 wt.-%. Suitable mixtures of polythiol and polyvinyl compounds and suitable filler-containing mixtures are described in WO 2005/086911. The quantity of initiator according to Formula (I) is preferably 0.05 to 0.5 wt.-%.

The subject of the invention is also the use of acylgermanes of Formula (I) for the preparation of adhesives, coatings, varnishes, inks, cements, composites, pre-shaped parts or dental materials and their use as initiators for radical polymerization.

The invention also relates to a process for the preparation of mouldings, in particular dental crowns, bridges, inlays and artificial teeth, in which a composition according to the invention is moulded into the moulding in per se known manner and then at least partially, preferably completely, cured. Curing preferably takes place through radical polymerization.

The photoinitiators according to the invention are characterized in particular by a high reactivity and a high activity already at low use concentration. An extremely rapid curing of the photopolymer can thereby be achieved compared with known photoinitiators which absorb in the visible range. For example, measurements of bisacyl diethylgermanium in a resin mixture of decanediol dimethacrylate ($D_3MA$):UDMA:bis-GMA=1:1:1 resulted in almost double the polymerization rate ($R_p$) of camphorquinone in combination with an amine accelerator in the same formulation. The curing time could likewise be halved compared with campherquinone/amine. Even with a 15-fold dilution of bisacyl diethylgermanium, a reactivity comparable with camphorquinone/amine as photoinitiator can still be achieved (see embodiment examples, Tables 7, 8, 9, sum of initiator and accelerator).

Moreover, the naturally yellow-coloured photoinitiators according to Formula (I) have an outstanding photobleaching effect, i.e. the compounds of Formula (I) are decolorized upon curing and discolorations of the material after curing are thereby avoided.

The invention is described in further detail below with reference to examples.

EXAMPLES

Example 1

Synthesis of benzoyltrimethylgermanium (Comparison Example)

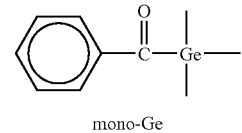

mono-Ge 1.64 g (4.49 mmol) allyl palladium(II)chloride dimer, 1.49 g (8.97 mmol) triethylphosphite and 23.24 g (98.7 mmol) hexamethyldigermanium were placed in a dry 50-ml three-necked flask with reflux condenser, magnetic stirrer and septum under argon and stirred for 5 min at room temperature. 12.62 g (89.7 mmol). 12.62 g (89.7 mmol) of freshly-distilled benzoyl chloride was then added dropwise. After stirring for 4 h at 110° C., the Pd catalyst was separated from the reaction mixture and volatile reaction products and the excess hexamethyldigermanium drawn off on the rotary evaporator. The reaction mixture was separated by column chromatography (PE:EE=40:1). 7.8 g (78% of the theoretical value) benzoyltrimethylgermanium (mono-Ge) was obtained as yellow liquid. DC (PE:EE=20:1): $R_f$=0.58.

UV-VIS: $\zeta_{max}$: 411.5 nm, $\epsilon$=1374 dm$^2$/mol $^1$H-NMR (400 MHz; CDCl$_3$): δ (ppm): 7.78-7.82 (m, 2H, Ar—H$^{2,6}$), 7.48-7.58 (m, 3H, Ar—H$^{3,4,5}$), 0.51 (s, 9H, —CH$_3$).

$^{13}$C-NMR (100 MHz; CDCl$_3$): δ (ppm): 234.39 (—C═O), 140.61 (Ar—C$^1$), 132.90 (Ar—C$^4$), 128.75 (Ar—C$^{2,6}$), 127.71 (Ar—C$^{3,5}$), −1.14 (—CH$_3$).

Example 2

Synthesis of
1,6-bis[4-(trimethylgermylcarbonyl)phenoxy]hexane

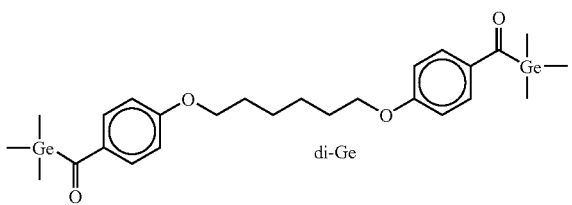
di-Ge

Stage 1: 1,6bis(4-formylphenoxy)hexane:

A mixture of 73.3 g (0.6 mol) p-hydroxybenzaldehyde, 73.2 g (0.3 mol) 1,6-dibromohexane, 39.6 g (0.6 mol) potassium hydroxide and 240 ml dimethylformamide was heated under reflux, accompanied by stirring for 1 h, in a 500 ml three-necked flask with reflux condenser, internal thermometer and magnetic stirrer. After cooling the reaction mixture to room temperature, the obtained crystal slurry was placed in a 2-1 beaker containing 1 l of deionized water. The formed suspension was stirred intensively by means of a mechanical stirrer until the initially increased temperature had returned to room temperature. The crystals present were then filtered off, washed thoroughly with water and the product recrystallized from a mixture of 1200 ml ethanol and 300 ml water. After drying to constant weight in the vacuum drying cupboard at 70-80° C. 63.5 g (65% of the theoretical value) 1,6-bis(4-formylphenoxy)hexane (m.p.: 109.8-111.2° C.) was obtained in the form of white crystals.

$^1$H-NMR (400 MHz; CDCl$_3$): δ (ppm): 9.88 (s, 2H, CHO), 7.84-7.81 (m, 4H, Ar—H$^{2,6}$), 7.01-6.98 (m, 4H, Ar—H$^{3,5}$), 4.06 (t, 4H, O—CH$_2$), 1.88-1.83 (m, 4H, O—CH$_2$—C$\underline{H}_2$) and 1.59-1.55 (m, 4H, CH$_2$).

Stage 2: 1,6-bis[4-(1,3-dithiane-2-yl)phenoxy]hexane:

A suspension of 52.55 g (0.16 mol) 1,6-bis(4-formylphenoxy)hexane, 200 ml chloroform and 34.85 g (0.32 mol) 1,3-propanedithiol was stirred in a 500-ml three-necked flask with gas-entry tube, reflux cooler, internal thermometer and magnetic stirrer and cooled to −10° C. Dry HCl gas was introduced for approx. 15 min, whereupon the suspension thickened markedly. After the introduction of the HCl was complete, the reaction mixture was stirred for another 30 min accompanied by ice-cooling, the ice bath was removed and the red-brown suspension was stirred for a further 2 h at room temperature. The solvent was then distilled off with a membrane pump (400 to 10 mbar) into a cold trap, 300 ml ethyl acetate and 100 ml methanol added to the residue and the reaction mixture stirred. The suspension was filtered, the solid residue washed with 100 ml methanol and 100 ml acetone and dried to constant weight in the vacuum drying cupboard. 78.2 g (96% of the theoretical value) 1,6-bis[4-(1,3-dithian-2-yl)phenoxy]hexane was obtained as a reddish, poorly soluble solid (m.p.: 189-192° C.).

1H-NMR (400 MHz; CDCl$_3$): δ (ppm): 7.39-7.26 (m, 4H, Ar—H$^{2,6}$), 6.86-6.83 (m, 4H, Ar—H$^{3,5}$), 5.13 (s, 2H, CH), 3.96 (t, 4H, O—CH$_2$), 3.09-2.87 (m, 8H, SCH$_2$) and 2.19-1.52 (m, 12H, 2×O—CH$_2$—C$\underline{H}_2$, 4×CH$_2$).

Stage 3: 1,6-bis{4-[2-(trimethylgermyl)-1,3-dithiane-2-yl]phenoxy}hexane:

A suspension of 8.11 g (16.0 mmol) 1,6-bis[4-(1,3-dithian-2-yl)phenoxy]hexane in 50 ml anhydrous tetrahydrofuran (THF) was prepared under argon in a dry 250-ml three-necked flask with 50 ml dropping funnel, internal thermometer, magnetic stirrer and septum. The suspension was cooled to −10° C. and 14.1 ml of a 2.5 molar solution of n-butyl lithium (35.2 mmol) in hexane added dropwise over a period of 10 min such that the internal temperature did not exceed 0° C. The brown solution was then stirred for 3 h at −10° C. and a solution of 4.90 g (32.0 mmol) trimethylgermanium chloride in 20 ml anhydrous THF added dropwise to it at −5° C. within 5 min. The reaction mixture was stirred for a further 24 h at room temperature. 50 ml water and 150 ml ethyl acetate were then added and the resultant phases separated. The organic phase was washed twice with 50 ml each time and the combined aqueous phases were re-extracted with 50 ml ethyl acetate. Finally, the combined organic phases were washed with 80 ml saturated aqueous NaCl solution and dried over anhydrous sodium sulphate. After separating off the desiccant, the reaction mixture was concentrated on the rotary evaporator and the product dried to constant weight under fine vacuum. 10.9 g (92% of the theoretical value) 1,6-bis{4-[2-(trimethylgermyl)-1,3-dithian-2-yl]phenoxy}hexane was obtained as a pale-yellowish solid (m.p.: 147-153° C.).

$^1$H-NMR (400 MHz; CDCl$_3$): δ (ppm): 7.78-7.76 (m, 4H, Ar—H$^{2,6}$), 6.91-6.88 (m, 4H, Ar—H$^{3,5}$), 3.99 (t, 4H, O—CH$_2$), 2.81-2.36 (m, 8H, SCH$_2$), 2.04-1.58 (m, 12H, 2×O—CH$_2$—C$\underline{H}_2$, 4×CH$_2$) and 0.18 (s, 18H, CH$_3$).

Stage 4: 1,6-bis[4-[2-(trimethylgermylcarbonyl)phenoxy]hexane:

3.70 g (5.0 mmol) 1,6-bis{4-[2-(trimethylgermyl)-1,3-dithian-2-yl]phenoxy}hexane was dissolved in 60 ml THF in a 250-ml two-necked flask with internal thermometer and magnetic stirrer. The whole synthesis including the purification operations was carried out in a yellow-light fume cupboard. 15 ml deionized water was added and a total of 12.01 g (0.12 mol) each of calcium carbonate and 30.46 g (0.12 mol) iodine added in approximately 8 equally large portions such that the time between the additions was approx. 30 min. The red-brown reaction mixture was stirred for a further 4 h at room temperature, filtered over a fritted-glass filter with a diameter of 5 cm, filled with 25 g silica gel 60 (0.035-0.070 mm), followed by washing with 100 ml THF. Approx. 200 ml saturated aqueous sodium dithionite solution was added to the filtrate until the colour changed to yellow. The suspension was then filtered and the filtration residue washed 4 times with 50 ml ethyl acetate each time. 800 ml ethyl acetate was added to the thus-obtained cloudy, yellow 2-phase mixture and the phases were separated. The organic phase was washed twice with 50 ml water each time and the combined water phases re-extracted with 50 ml ethyl acetate. The combined organic phases were washed with 80 ml saturated aqueous NaCl solution and dried over anhydrous sodium sulphate. After separating the desiccant, the reaction mixture was concentrated on the rotary evaporator and the product dried under fine vacuum. 20 ml dichloromethane was added to the oily, red-brown solid that was left which was filtered over a fritted-glass filter with a diameter of 5 cm, filled with 40 g silica gel 60 (0.035-0.070 mm), and washed with 800 ml dichloromethane. The eluent was concentrated on the rotary evaporator and dried to constant weight under fine vacuum (0.06 mbar) at 50° C. The now-obtained red-brown solid of approx. 2 g was dissolved in 10 ml dichloromethane and purified by means of flash column chromatography: column: 75 g silica gel 60 (0.035-0.070 mm), 2.5 cm diameter, eluent dichloromethane. After approx. 100 ml forerun and 400 ml intermediate run 1100 ml main fraction is collected, concentrated on the rotary evaporator and dried to constant weight under fine vacuum (0.06 mbar) at 50° C. 1.20 g (43% of the theoretical value) 1,6-bis[4-[2-(trimethylgermylcarbonyl)phenoxy]hexane (di-Ge) was obtained as a pale-yellow solid (m.p.: 85.0-86.4° C.).

$^1$H-NMR (400 MHz; $CDCl_3$): δ (ppm): 7.80-7.78 (m, 4H, Ar—H$^{2,6}$), 6.97-6.94 (m, 4H, Ar—H$^{3,5}$), 4.04 (t, 4H, O—$CH_2$), 1.68-1.64 (m, 4H, O—$CH_2$—C$\underline{H}_2$), 1.57-1.55 (m, 4H, $CH_2$) and 0.49 (s, 18H, $CH_3$).

$^{13}$C-NMR (100 MHz; $CDCl_3$): δ (ppm): 231.13 (—C=O), 162.82 (Ar—C$^1$), 134.35 (Ar—C$^4$), 129.97 (Ar—C$^{2,6}$), 114.28 (Ar—C$^{3,5}$), 67.95 (O—$CH_2$), 28.93 (O—$CH_2$—C$\underline{H}$), 25.70 ($CH_2$) and −1.12 (—$CH_3$).

The photoinitiator di-Ge according to the invention with a long-wave absorption maximum of 400.5 nm has an extinction coefficient ε=3260 dm$^2$/mol which is thus more than twice that of benzoyltrimethylgermane mono-Ge (ε=1461 dm$^2$/mol), which leads to an improvement in photopolymerization activity. Compared with the Norrish type II photoinitiator camphorquinone widely used in the dental field, the extinction coefficient of which ε at $\lambda_{max}$ of 468 nm is only 380 dm$^2$/mol and which moreover requires an additional reducing agent, in most cases amine, for effective radical formation, the absorption maximum of di-Ge is clearly on a shorter wavelength and thus fades very well when irradiated.

Example 3

Preparation of a Composite Cement Using the di-Ge from Example 2

Composite fixing cements based on a methacrylate mixture and incorporating either different concentrations of the photoinitiator di-Ge (cements A and B), benzoyltrimethylgermane mono-Ge from Example 1 (cement C, comparison) or a mixture of camphorquinone and p-N,N-dimethylaminobenzoic acid ethyl ester (cement D, comparison) were prepared by means of an "Exakt" roll mill (Exakt Apparatebau, Norderstedt) according to Table 1 below. Cements B, C and D contain the same molar concentration of photoinitiator, i.e. benzoyltrimethylgermane (cement C) or camphorquinone (cement D). Corresponding testpieces were prepared from the materials, irradiated twice for 3 minutes with a dental light source (Spectramat®, Ivoclar Vivadent AG) and thus cured. The bending strength, bending E modulus and the exothermic time were measured according to the ISO standard ISO-4049 (Dentistry—Polymer-based filling, restorative and luting materials).

It can be seen from Table 2 that the di-Ge-based cements produce a better curing as photoinitiator concentration increases. It can be seen that cement B with di-Ge as photoinitiator results in composites with better mechanical properties compared with cement C, based on mono-Ge or cement D, based on a conventional photoinitiator mixture of camphorquinone and p-N,N-dimethylaminobenzoic acid ethyl ester.

TABLE 1

Composition of the composite cements (wt.-%)

| Component | Cement A | Cement B | Cement C[1] | Cement D[1] |
|---|---|---|---|---|
| Di-Ge | 0.34 | 1.01 | — | — |
| Mono-Ge from Example 1 | — | — | 0.32 | — |
| Camphorquinone | — | — | — | 0.24 |
| p-N,N-dimethylaminobenzoic acid ethyl ester | — | — | — | 0.23 |
| UDMA[2] | 31.87 | 31.20 | 31.89 | 31.80 |
| Triethyleneglycol dimethacrylate | 7.81 | 7.81 | 7.81 | 7.81 |
| Aerosil OX-50 (Degussa) | 41.27 | 41.27 | 41.27 | 41.23 |
| Ytterbium trifluoride (Rhone-Poulenc) | 18.71 | 41.27 | 18.71 | 18.69 |

[1] Comparison example
[2] Addition product of 2 mol 2-hydroxyethylmethacrylate and 1 mol 2,2,4-trimethylhexamethylene diisocyanate

TABLE 2

Composite cement properties

| Component | Cement A | Cement B | Cement C[1] | Cement D[1] |
|---|---|---|---|---|
| Exothermic time (s) | 11 | 10 | 12 | 8 |
| Bending strength (MPa) after 24 h WI[2] | 115 | 124 | 116 | 118 |
| E modulus (MPa) after 24 h WI[1] | 5930 | 6570 | 5240 | 5580 |

[1] Comparison example
[2] WI = water immersion of the testpieces at 37° C.

Example 4

Preparation of a Filling Composite Using the di-Ge from Example 2

Filling composites based on a methacrylate mixture and incorporating the same molar concentrations of the photoinitiator di-Ge (composite F) according to the invention, benzoyltrimethylgermane mo-Ge (comparison) from Example 1 (composite G) or a mixture of campherquinone and p-N,N-dimethylaminobenzoic acid ethyl ester (composite G) were prepared using an LPM 0.1 SP kneader (Linden, Marienheide) according to Table 3 below. Analogous to Example 2, testpieces were prepared from the materials and cured. The bending strength, bending E modulus were measured according to the ISO standard ISO-4049. The results shown in Table 4 show a significantly better curing of the composites with the photoinitiator di-Ge according to the invention compared with conventional camphorquinone-based initiator systems or acylgermanium compounds with a Ge atom in the molecule.

TABLE 3

Composition filling composite (wt.-%)

| Component | Composite E | Composite F[1] | Composite G[1] |
|---|---|---|---|
| Monomer resin[2] | 18.14 | 18.06 | 17.99 |
| Di-Ge | 0.19 | — | — |
| Mono-Ge | — | 0.08 | — |
| Camphorquinone | — | — | 0.05 |
| p-N,N-dimethylaminobenzoic acid ethyl ester | — | — | 0.09 |
| Glass filler GM27884 (Schott)[3] | 51.61 | 51.61 | 51.61 |

TABLE 3-continued

| | Composition filling composite (wt.-%) | | |
|---|---|---|---|
| Component | Composite E | Composite F[1] | Composite G[1] |
| Spherosil (Tokoyama Soda)[4] | 14.36 | 14.37 | 14.36 |
| Ytterbium trifluoride (Rhone-Poulenc) | 14.89 | 14.89 | 14.89 |
| OX-50[4] | 0.81 | 0.99 | 1.01 |

[1] Comparison example
[2] Mixture of 42.4 wt.-% bis-GMA, 37.4 wt.-% UDMA and 20.2 wt.-% triethyleneglycol dimethacrylate
[3] Silanized Ba—Al-boron silicate glass filler with an average particle size of 1.5 μm,
[4] $SiO_2$—$ZrO_2$ mixed oxide (average primary particle size: 250 nm)
[4] Silanized pyrogenic $SiO_2$ OX-50 (Degussa)

TABLE 4

| | Filling composite properties | | |
|---|---|---|---|
| Material property | Composite E | Composite F[1] | Composite G[1] |
| Exothermic time (s) | 3.6 | 10 | 9 |
| Bending strength (MPa) after 24 h WI[2] | 173 | 150 | 168 |
| Bending E modulus (GPa) after 24 h WI[2] | 14370 | 10540 | 12190 |

[1] Comparison example
[2] WI = water immersion of the testpieces at 37° C.

Example 5

Synthesis of 1,6-bis[4-(benzoyldiethylgermyl)carbonyl)-phenoxy]hexane

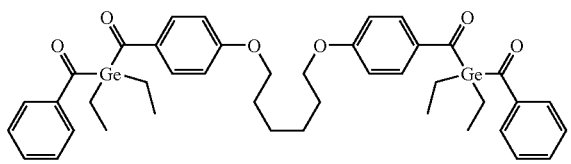

Stage 1: Chlorodiethyl(2-phenyl-1,2-dithian-2-yl)germanium:

19.63 g (0.10 mol) 2-phenyl-1,3-dithian was dissolved under argon in 200 ml anhydrous tetrahydrofuran (THF) in a dry 500-ml three-necked flask with 50 ml dropping funnel, internal thermometer, magnetic stirrer and septum. The solution was cooled to −10° C. 44 ml of a 2.5 molar solution of n-butyllithium (0.11 mol) in n-hexane was added dropwise at −5° C. over a period of 50 min. After the addition was complete, the green solution was stirred for 2 h at 0° C. It was then added dropwise within 45 min to a solution, cooled to −72° C., of 20.16 g (0.10 mol) diethylgermanium dichloride in 500 ml anhydrous THF, wherein the temperature did not exceed −65° C. The reaction mixture was stirred for a further 16 h in a thawing cold bath, then concentrated on the rotary evaporator. 100 ml dry n-hexane was added to the residue followed by stirring for 1 h at room temperature. The suspension was filtered and the filtrate was concentrated on the rotary evaporator and dried under fine vacuum. The oily, yellow crude product was purified by means of high-vacuum distillation (b.p.: 135-150° C./4×10$^{-5}$ mbar). 27.23 g (75% of the theoretical value) chlorodiethyl(2-phenyl-1,3-dithian-2-yl)germanium was obtained as a yellow oil.

$^1$H-NMR (400 MHz; CDCl$_3$): δ (ppm): 7.99-8.01 (m, 2H, Ar—H$^{3,5}$), 7.38-7.42, (m, 2H, Ar—H$^{2,6}$), 7.20-7.25 (m, 1H, Ar—H$^4$), 2.79-2.86 and 2.44-2.49 (m, 2×2H, CH$_2$S), 2.04-2.15 and 1.89-1.93 (m, 2×1H, CH$_2$CH$_2$CH$_2$), 1.17-1.29 (m, 4H, CH$_2$CH$_3$), 1.03-1.10 (m, 6H, CH$_3$).

Stage 2: 1,6-bis-{[4-(2-diethyl-2'-phenyl-1',3'-dithian-2'-yl-germyl)-1,3-dithian-2-yl]phenoxy}hexane:

100 ml anhydrous THF was added under argon to 8.11 g (16.0 mmol) 1,6-bis[4-(1,3-dithian-2-yl)phenoxy]hexane (Example 2, stage 2) in a dry 250-ml three-necked flask with 50 ml dropping funnel, internal thermometer, magnetic stirrer and septum. The suspension was cooled to −10° C. 14.1 ml of a 2.5 molar solution of n-butyllithium (35.2 mmol) in n-hexane was added dropwise within 15 min such that the temperature of the reaction mixture did not exceed 0° C. After the addition was complete, the brown solution was stirred for 3 h at −10° C. A solution of 11.57 g (32.0 mmol) chlorodiethyl (2-phenyl-1,3-dithian-2-yl)germanium in 40 ml dry THF was then added dropwise within 15 min at −5° C. The reaction mixture was stirred for a further 16 h at room temperature. 50 ml water and 150 ml ethyl acetate were then added and the phases were separated. The organic phase was washed twice with 50 ml water each time and the combined aqueous phases were re-extracted with 80 ml ethyl acetate. The combined organic phases were washed with 100 ml saturated aqueous NaCl solution and dried over anhydrous sodium sulphate. After separating the desiccant, the reaction mixture was concentrated on the rotary evaporator and the residue dried to constant weight under fine vacuum. The crude product was purified by means of column chromatography (SiO$_2$, dichloromethane). 12.90 g (70% of the theoretical value) 1,6-bis-{[4-(2-diethyl-2'-phenyl-1',3'-dithian-2'-yl-germyl)-1,3-dithian-2-yl]phenoxy}hexane was obtained as a pale-yellowish foam.

$^1$H-NMR (400 MHz; CDCl$_3$): δ (ppm): 7.95 and 7.78 (d, 2×4H, Ar—H), 7.25-7.31 and 7.12-7.15 (m, 4H+2H, Ar—H), 6.82 (d, 4H, Ar—H), 4.00 (t, 4 H, CH$_2$O), 2.69-2.79 and 2.22-2.30 (m, 2×8H, CH$_2$S), 1.72-2.05 (m, 12H, OCH$_2$CH$_2$+SCH$_2$CH$_2$), 1.56-1.61 (m, 4H, OCH$_2$CH$_2$CH$_2$), 1.25-1.32 (m, 8H, CH$_2$CH$_3$), 1.10-1.16 (m, 12H, CH$_3$).

Stage 3: 1,6-bis-{4-[enzoyl-diethylgermyl)carbonyl]phenoxy}hexane:

7.90 g (6.8 mmol) 1,6-bis-{[4-(2-diethyl-2'-phenyl-1',3'-dithian-2'-yl-germyl)-1,3-dithian-2-yl]phenoxy}hexane was dissolved in 120 ml THF in a 250-ml brown glass two-necked flask with internal thermometer and magnetic stirrer (the whole synthesis including the purification operations was carried out under yellow light). 30 ml deionized water was added to the solution. A total of 16.40 g (0.16 mol) calcium carbonate and 41.60 g (0.16 mol) iodine was added in eight approximately equal portions such that the time between the additions was approx. 30 min. The reaction was monitored by HPLC. To ensure a complete reaction, in total a further 6 g calcium carbonate and 15 g iodine were added. After 24 h the red-brown reaction mixture was filtered over a fritted-glass filter filled with silica gel. The reaction mixture was then re-washed with 150 ml THF. Approx. 200 ml saturated aqueous sodium dithionite solution was then added to the filtrate until the colour changed to yellow. The suspension was then filtered and the filtration residue washed with 300 ml ethyl acetate. The two phases of the filtrate were separated. The organic phase was washed twice with 100 ml water each time and the combined water phases were re-extracted with 100 ml ethyl acetate. The combined organic phases were washed with 100 ml saturated aqueous NaCl solution and dried over anhydrous sodium sulphate. After separating the desiccant, the reaction mixture was concentrated on the rotary evaporator and the residue was dried under fine vacuum. The oily, yellow crude product was purified by means of column chromatography (SiO$_2$, n-hexane/ethyl acetate 9:1). 1.74 g (32% of the theoretical value) 1,6-bis-{4-[(benzoyl-diethylgermyl)carbonyl]phenoxy}hexane was obtained as a yellow solid (m.p.: 78-80° C.).

$^1$H-NMR (400 MHz; CDCl$_3$): δ (ppm): 7.68-7.76 (m, 8H, Ar—H), 7.46-7.52 (m, 2H, Ar—H), 7.38-7.44 and 6.85-6.89 (m, 2×4H, Ar—H), 3.97 (m, 4H, CH$_2$O), 1.77-1.80 (4H, OCH$_2$CH$_2$), 1.44-1.51 (m, 12H, OCH$_2$CH$_2$CH$_2$+CH$_2$CH$_3$), 1.11 (t, 12H, CH$_3$).

$^{13}$C-NMR (100 MHz; CDCl$_3$): δ (ppm): 230.7 and 226.6 (C=O), 163.3, 141.1, 134.8, 133.4, 130.5, 128.8, 128.0, 114.5 (all Ar—C), 68.1 (CH2O), 28.9 and 25.7 (OCH$_2$CH$_2$), 8.98 (CH$_3$) 6.43 (CH$_2$CH$_3$).

Example 6

Synthesis of 22,45-digerma-22,22,45,45-tetraethyl-7,14,30,37-tetraoxa-21,23,44,46-tetraoxo[8.3.8.3](1,4) (1,4) (1,4) (1,4)cyclophane

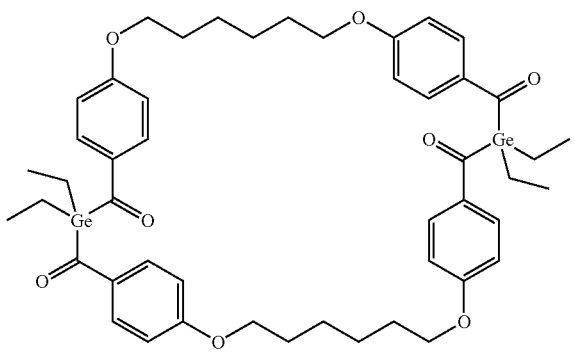

Stage 1: 22,45-digerma-22,22,45 45-tetraethyl-7,14,30,37-tetraoxa-21,23,44,46-tetrakis(2-phenyl-1,3-dithian-2-yl)[8.3.8.3](1,4) (1,4) (1,4) (1,4)cyclophane:

800 ml anhydrous tetrahydrofuran (THF) was added under argon to 40.55 g (80.0 mmol) 1,6-bis[4-(1,3-dithian-2-yl)phenoxy]hexane (Example 2, stage 2) in a dry 2-1 three-necked flask with 250-ml dropping funnel, internal thermometer, magnetic stirrer and septum. The suspension was cooled to −5° C. 70.4 ml of a 2.5-molar solution of n-butyllithium (0.176 mol) in n-hexane was added dropwise over 1 h such that the temperature of the reaction mixture did not exceed 0° C. After the addition was complete, the brown solution was stirred for 3 h at −5° C. A solution of 16.13 g (80.0 mmol) diethylgermanium dichloride in 200 ml was then added dropwise to dry THF over 2 h at −5° C. The reaction mixture was stirred for a further 16 h at room temperature. 200 ml water and 500 ml ethyl acetate were then added. A precipitated oily, brown material was separated off and discarded. The obtained phases were separated. The organic phase was washed twice with 200 ml water each time and the combined aqueous phases were re-extracted with 200 ml ethyl acetate. The combined organic phases were washed with 200 ml saturated aqueous NaCl solution and dried over anhydrous sodium sulphate. After the desiccant was separated off, the reaction mixture was concentrated on the rotary evaporator and the residue dried to constant weight under fine vacuum. The crude product was dissolved in 750 ml dichloromethane by heating under reflux and hot-filtered. The filtrate was concentrated to approximately a third of the volume. The solid formed after cooling was filtered off, washed twice with 20 ml dichloromethane each time and dried to constant weight in the vacuum drying cupboard. 7.95 g (16% of the theoretical value) 22,45-digerma-22,22,45,45-tetraethyl-7,14,30,37-tetraoxa-21,23,44,46-tetrakis(2-phenyl-1,3-dithian-2-yl)[8.3.8.3](1,4) (1,4) (1,4) (1,4)cyclophane was obtained as a white solid (m.p.: 260-262° C.).

$^1$H-NMR (400 MHz; CDCl$_3$): δ (ppm): 7.41 and 6.58 (d, 2×8H, Ar—H), 3.96 (t, 8H, CH$_2$O), 2.68-2.78 and 2.25-2.33 (m, 2×8H, CH$_2$S), 1.74-2.05 (m, 16H, CH$_2$CH$_2$O+CH$_2$CH$_2$S), 1.60-1.69 (m, 8H, CH$_2$CH$_2$CH$_2$O), 1.41-1.54 (m, 20H, CH$_2$CH$_3$.

Stage 2: 22,45-digerma-22,22,45,45-tetraethyl-7,14,30,37-tetraoxa-21,23,44,46-tetraoxo[8.3.8.3](1,4) (1,4) (1,4) (1,4)cyclophane:

60 ml THF and 15 ml deionized water were added to 2.54 g (2.0 mmol) 22,45-digerma-22,22,45,45-tetraethyl-7,14,30,37-tetraoxa-21,23,44,46-tetrakis(2-phenyl-1,3-dithian-2-yl)[8.3.8.3](1,4)(1,4) (1,4) (1,4)cyclophane in a 250-ml brown glass two-necked flask with internal thermometer and magnetic stirrer (the whole synthesis including the purification operations was carried out under yellow light). In total 4.80 g (48.0 mmol) calcium carbonate and 12.18 g (48.0 mmol) iodine were added in eight approximately equal portions such that the time between the additions was approx. 30 min. The suspension was stirred for a total of 24 h at room temperature. The red-brown reaction mixture was then filtered over a fritted-glass filter filled with silica gel. The reaction mixture was washed again with 50 ml acetone. Approx. 50 ml saturated aqueous sodium dithionite solution was added to the filtrate until the colour changed to yellow. The suspension was then filtered and the filtration residue washed with 200 ml ethyl acetate. The two phases of the filtrate were separated. The organic phase was washed twice with 50 ml water each time and the combined water phases were re-extracted twice with 50 ml ethyl acetate each time. The combined organic phases were washed with 100 ml saturated aqueous NaCl solution and dried over anhydrous sodium sulphate. After the desiccant was separated off, the reaction mixture was concentrated on the rotary evaporator and the residue was dried under fine vacuum. The oily, yellow solid was purified by means of column chromatography (SiO$_2$, dichloromethane). 22,45-digerma-22,22,45,45-tetraethyl-7,14,30,37-tetraoxa-21,23,44,46-tetraoxo[8.3.8.3](1,4) (1,4) (1,4) (1,4)cyclophane was obtained as a yellow solid (m.p.: 162-164° C.).

$^1$H-NMR (400 MHz; CDCl$_3$): δ (ppm): 7.67 and 6.83 (d, 2×8H, Ar—H), 3.95 (t, 8H, CH$_2$O), 1.71-1.81 (m, 8H, CH$_2$CH$_2$O), 1.39-1.50 (m, 16H, CH$_2$CH$_2$CH$_2$O+CH$_2$CH$_3$), 1.05-1.15 (t, 12H, CH$_3$).

$^{13}$C-NMR (100 MHz; CDCl$_3$): δ (ppm): 227.5 (C=O), 163.2, 134.8, 130.5, 114.5 (all Ar—C), 67.73 (CH2O), 28.7 and 25.3 (CH$_2$CH$_2$CH$_2$O), 9.00 (CH$_3$), 6.04 (CH$_2$CH$_3$).

Although various embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

The invention claimed is:

1. A composition comprising at least one polymerizable binder and at least one acylgermanium compound according to general Formula (I),

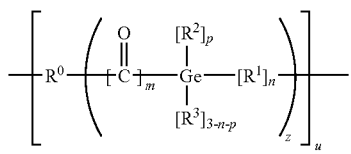
Formula (I)

in which
u is 1 and the two y1-positions at $R^0$ and $R^1$ are dispensed with,
z is an integer of 2 to 10,
wherein
$R^0$ is a z-valent branched or linear aliphatic, aromatic or aliphatic-aromatic hydrocarbon radical with 1 to 50 carbon atoms and 0 to 10 hetero atoms, which is substituted z times by the group in round brackets, wherein if z=2 or 3 $R^0$ can also be N or NH, N—$C_{1-3}$-alkyl or N-phenyl, and wherein if z=2 and m=0 $R^0$ can also be dispensed with, with the result that two of the groups in round brackets are connected to each other by a chemical bond between the germanium atoms, and wherein the radical $R^0$ can be substituted by one or more oxygen atoms (=O), CN, halogen, one or more branched or linear $C_{1-6}$ alkyl radicals, —O—$C_{1-6}$-alkyl radicals and/or polymerizable groups;
$R^1$, $R^2$ independently of each other are

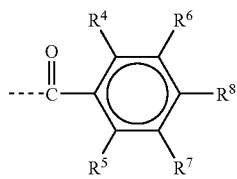

or H or have one of the meanings given for $R^3$; wherein
$R^4$, $R^5$ independently of each other are in each case H, halogen, a branched or linear $C_{1-6}$ alkyl or —O—$C_{1-6}$-alkyl radical which can be interrupted by one or more oxygen atoms;
$R^6$, $R^7$, $R^8$ independently of each other are in each case H, halogen, a branched, cyclic or preferably linear $C_{1-20}$ alkyl, -alkenyl, -alkyloxy or -alkenoxy radical, which can be interrupted by one or more O, S or —$NR^{20}$— and can be substituted by one or more polymerizable groups and/or radicals $R^9$, wherein $R^9$ is —OH, —$C_xF_{2x+1}$ with x=1 to 20, —$[Si(CH_3)_2]_y$—$CH_3$ with y=1 to 20, and $R^{20}$ is H, halogen, a branched, cyclic or preferably linear $C_{1-20}$ alkyl, -alkenyl, -alkyloxy or -alkenoxy radical, and
wherein $R^2$ can also be a linear or branched aliphatic, aromatic or aliphatic-aromatic hydrocarbon radical with 1 to 50 carbon atoms and 0 to 10 hetero atoms, which forms a bridge between two germanium atoms,
and wherein the other variables have the following meanings:
m is 0 or 1,
n is 0 or 1,
p is 0 or 1,
$R^3$ is a branched or linear $C_{1-18}$ alkyl radical or $C_{2-18}$ alkenyl radical, wherein these radicals can be unsubstituted or substituted one or more times by a radical which is selected from the following group:

halogen, CN, 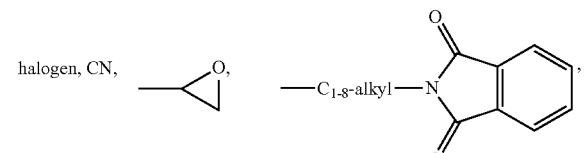

—$OR^{10}$, —$SR^{10}$, —$OCO$—$R^{10}$, —$COO$—$R^{10}$, —$CH=CH$—$CO$—$OR^{10}$, —$C(C_{1-4}$-alkyl)=$C(C_{1-4}$-alkyl)-$CO$—$OR^{10}$, —$CO$—$R^{13}$, —$CO$—$CH=CH$—$CO$—$C_{1-6}$-alkyl, —$CO$—$CH=CH$—$CO$-phenyl, —$CO$—$CH=CH$—$COO$—$C_{1-18}$-alkyl, —$NR^{11}R^{12}$, —$N(R^{11})$—$CO$—$R^{10}$, —$N(R^{11})$—$COO$—$R^{10}$, —$N(R^{11})$—$CO$—$NR^{11}R^{12}$, —$N(R^{11})$—$CO$-hal, —$CO$—$NR^{11}R^{12}$, —$SO_2$—$R^{10}$, —$SO_2$—$OR^{10}$, —$SO_2$—$NR^{11}R^{12}$, —$PO(OC_{1-8}$-alkyl)$_2$, —$SiR^{14}R^{15}R^{16}$, —$CH=CH$-phenyl, —$C(C_{1-4}$-alkyl)=$C(C_{1-4}$-alkyl)phenyl, phenyl-$C_{1-4}$-alkyl, phenyl, naphthyl, biphenyl, $C_{5-12}$-cycloalkyl, a saturated or unsaturated 5 or 6-membered O—, S— or N-containing heterocyclic ring, benzophenonyl, thisanthonyl, wherein
$R^{10}$ is H; $C_{1-18}$ alkyl, $C_{1-18}$ alkyl which is interrupted by one or more oxygen atoms; $C_{2-18}$ alkenyl; $C_{2-18}$ alkenyl, which is interrupted by one or more oxygen atoms; $C_{3-12}$ cycloalkyl; tetrahydropyran-2-yl, phenyl-$C_{1-20}$-alkylene; phenyl-$C_{1-20}$-alkenylene; $C_{1-6}$ alkyl which can be unsubstituted or substituted by halogen, cyclohexyl, cyclopentyl, tetrahydrofuranyl, furanyl or isopropyl-4-methyl-cyclohexyl; is phenyl, naphthyl or biphenyl, wherein these ring systems can be unsubstituted or substituted by 1 to 5 halogen atoms; $C_{1-8}$ alkyl, $C_{1-8}$ alkoxy and/or $C_{1-8}$ alkylthio radicals;
$R^{11}$, $R^{12}$ independently of each other are H; $C_{1-18}$ alkyl, $C_{1-18}$ alkyl which is interrupted by one or more oxygen atoms; $C_{2-18}$ alkenyl, $C_{2-18}$ alkenyl which is interrupted by one or more oxygen atoms; $C_{3-12}$ cycloalkyl, phenyl-$C_{1-4}$-alkyl; phenyl; naphthyl or pyridyl; wherein these ring systems can be unsubstituted or substituted by 1 to 5 halogen atoms, $C_{1-8}$ alkyl, $C_{1-8}$ alkoxy and/or $C_{1-8}$ alkylthio radicals; or $R^{11}$ and $R^{12}$ together form a 5 or 6-membered O—, S— or N-containing heterocyclic ring which for its part can be anellated with an aliphatic or aromatic ring;
$R^{13}$ is $C_{1-18}$ alkyl, $C_{2-18}$ alkenyl which is interrupted by one or more O atoms, $C_{3-12}$ cycloalkyl, phenyl-$C_{1-4}$-alkyl, phenyl, naphthyl or biphenyl, wherein said ring systems can be unsubstituted or substituted by 1 to 5 $C_{1-8}$ alkyl, $C_{1-8}$ alkoxy, $C_{1-8}$ alkylthio radicals and/or halogen atoms;
$R^{14}$, $R^{15}$, $R^{16}$ independently of each other are in each case H, $C_{1-8}$ alkyl, $C_{2-8}$ alkenyl, $C_{7-9}$ phenylalkyl, —O—$C_{1-8}$-alkyl, phenyl or —O—$SiR^{17}R^{18}R^{19}$, wherein
$R^{17}$, $R^{18}$, $R^{19}$ independently of each other are in each case H, $C_{1-8}$ alkyl, $C_{2-8}$ alkenyl, $C_{7-9}$ phenylalkyl, —O—$C_{1-8}$-alkyl or phenyl,
wherein in each case two of the radicals $R^1$, $R^2$ or $R^3$ can be connected to each other to form a 5- to 8-membered ring which for its part can be anellated with one or more aliphatic or aromatic rings, wherein these rings can contain further hetero atoms in addition to the germanium atom, and wherein different radicals, or in the case of m, n, p or 3-n-p>1 also identical radicals, can be connected to each other to form one or more rings, and wherein the formed rings can be unsubstituted or substituted one or more times.

2. The composition according to claim 1, which comprises at least one compound according to Formula (I'),

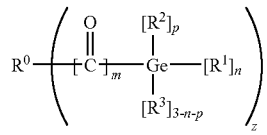

Formula (I')

in which

R⁰ is an alkyl group with 1 to 6 carbon atoms, wherein z hydrogen atoms of this group are substituted by the bracket term of Formula (I'), $R^1$, $R^2$ independently of each other are

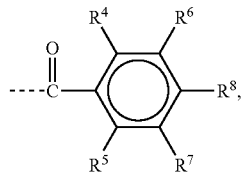

or H or have one of the meanings given for $R^3$, wherein $R^4$, $R^5$ independently of each other are in each case H, halogen, a branched or linear $C_{1-6}$ alkyl or —O—$C_{1-6}$-alkyl radical;

$R^6$, $R^7$, $R^8$ independently of each other are in each case H, halogen, a branched, cyclic or preferably linear $C_{1-20}$ alkyl, -alkenyl, -alkyloxy or -alkenoxy radical which can be interrupted by one or more O, S or —NR'— and can be substituted by one or more polymerizable groups and/or radicals $R^9$, wherein R' is H, halogen, a branched, cyclic or preferably linear $C_{1-20}$ alkyl, -alkenyl, -alkyloxy or -alkenoxy radical;

$R^3$, or is a branched or preferably linear $C_{1-18}$ alkyl, -alkenyl, -alkoxy or -alkenoxy radical which can be interrupted one or more times by O, m is 0 or 1, n is 0 or 1, p is 0 or 1;

z is 2 to 6.

3. A composition comprising at least one polymerizable binder and at least one acylgermanium compound according to general Formula (II),

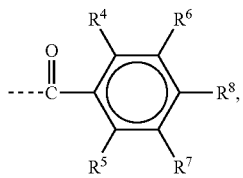

Formula (II)

in which $R^1$, $R^2$, $R^3$ independently of each other are

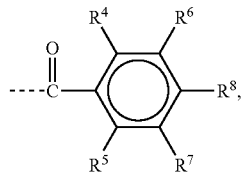

a $C_{1-3}$ alkyl radical or a $C_{1-3}$ acyl group;

$R^4$, $R^5$ independently of each other are in each case H, halogen, a linear or branched $C_{1-6}$ alkyl or —O—$C_{1-6}$-alkyl radical;

$R^6$, $R^7$, $R^8$ independently of each other are in each case H, halogen, a branched, cyclic or preferably linear $C_{1-20}$ alkyl, -alkenyl, -alkyloxy or -alkenoxy radical which is interrupted one or more times by O, S or —$NR^{20}$— and can be substituted by one or more polymerizable groups and/or radicals $R^9$;

$R^9$ is —OH, —$C_xF_{2x+1}$ with x=1 to 20, —[Si(CH₃)₂]ᵧ—CH₃ with y=1 to 20; and $R^{20}$ is H, halogen, a branched, cyclic or preferably linear $C_{1-20}$ alkyl, -alkenyl, -alkyloxy or -alkenoxy radical.

4. The composition according to claim 1 in which the radicals $R^2$, $R^3$, $R^6$, $R^7$ and $R^8$ are in each case substituted with 1 to 3 polymerizable groups.

5. The composition according to claim 1, in which the polymerizable groups are selected from vinyl, styryl, (meth)acrylate, (meth)acrylamide or N-alkylacrylamide.

6. The composition according to claim 1, which contains, relative to the total mass of the composition, 0.001 to 5 wt.-% of the acylgermanium compound.

7. The composition according to claim 1, which contains as polymerizable binder at least one of a radically polymerizable monomer and a prepolymer.

8. The composition according to claim 7, which contains as binder a mono- or multifunctional (meth)acrylate or a mixture thereof.

9. The composition according to claim 7, which contains at least one radically ring-opening polymerizable monomer.

10. The composition according to claim 1, which contains as binder a mixture of at least one of a mono- and multifunctional mercapto compounds and di- and multifunctional unsaturated monomers.

11. The composition according to claim 1, which contains at least one further initiator for radical polymerization.

12. The composition according to claim 1, which contains at least one further initiator for cationic polymerization.

13. The composition according to claim 1, which also contains filler.

14. The composition according to claim 1, which also contains at least one additive which is selected from stabilizers, UV absorbers, slip additives, wetting agents, dispersants, adhesion promoters, matting and brightening agents, levelling agents and film-forming auxiliaries, antiskinning agents, light-protection agents, corrosion-protection agents, flame retardants, antioxidants, optical brighteners, flow improvers, thickeners and anti-foaming agents.

15. The composition according to claim 1, which contains 0.001 to 5 wt.-% acylgermanium compound, 5 to 99.9 wt.-% polymerizable binder, 0 to 90 wt.-% filler, relative in each case to the total mass of the composition.

16. The composition according to claim 15, which contains 0 to 50 wt.-% of further additive.

17. A system for the preparation of mouldings, which contains a composition according to claim 1 and an LED light source.

18. The system according to claim 17, in which the LED light source has a wavelength in the range from 400 to 550 nm and the acylgermanium compound has an activation wavelength in the range from 400 to 550 nm.

19. A process for the preparation of a moulding comprising molding a composition according to claim 1 into a body with the desired shape and then completely or partially curing the body.

20. The process according to claim 19, in which the moulding is cured by irradiation with light of a wavelength of 200 to 700 nm.

21. The process according to claim 20, in which the moulding is cured by irradiation with light of a wavelength of 300 to 550 nm.

22. The process according to claim 20, in which the moulding is cured by irradiation with light of a wavelength of 400 to 800 nm.

23. The process according to claim 19 wherein the moulding comprises dental crowns, bridges, inlays or artificial teeth.

* * * * *